United States Patent [19]

Ullman

[11] Patent Number: 5,332,662

[45] Date of Patent: Jul. 26, 1994

[54] METHODS FOR DETERMINING PEROXIDATIVELY ACTIVE SUBSTANCES

[75] Inventor: Edwin F. Ullman, Atherton, Calif.

[73] Assignee: Syntex (U.S.A.) Inc., Palo Alto, Calif.

[21] Appl. No.: 923,080

[22] Filed: Jul. 31, 1992

[51] Int. Cl.$^5$ .................... C12Q 1/28; G01N 33/542; G01N 33/536

[52] U.S. Cl. .................... 435/28; 436/537; 436/534; 435/25; 435/7.1; 435/19; 435/188; 435/810; 536/4.1; 536/17.2; 536/17.9

[58] Field of Search .................. 435/28, 19, 25, 4, 7.1, 435/810, 188; 436/537, 534; 536/4.1, 17, 17.9

[56] References Cited

U.S. PATENT DOCUMENTS

| | | | |
|---|---|---|---|
| 3,527,331 | 9/1970 | Deutsch | 195/103.5 |
| 4,233,402 | 11/1980 | Maggio et al. | 436/537 |
| 4,256,834 | 3/1981 | Zuk et al. | 436/537 |
| 4,277,437 | 7/1981 | Maggio | 436/537 |
| 4,279,992 | 7/1981 | Boguslaski et al. | 435/19 |
| 4,279,993 | 7/1981 | Boguslaski et al. | 435/7 |
| 4,310,626 | 1/1982 | Burkhardt et al. | 435/28 |
| 4,318,707 | 3/1982 | Litman et al. | 436/537 |
| 4,391,905 | 7/1983 | Bauer | 435/14 |
| 4,391,906 | 7/1983 | Bauer | 435/14 |
| 4,556,640 | 12/1985 | Gantzer | 436/66 |
| 4,587,220 | 5/1986 | Mayambala-Mwanika et al. | 436/66 |
| 4,596,770 | 6/1986 | Parham et al. | 435/7 |
| 4,615,972 | 10/1986 | Gallacher | 435/28 |
| 4,654,300 | 3/1987 | Zuk et al. | 436/534 |
| 4,789,630 | 12/1988 | Bloch et al. | 435/7 |
| 4,853,328 | 8/1989 | Okazaki et al. | 435/28 |
| 4,891,314 | 1/1990 | Pauly et al. | 435/28 |

FOREIGN PATENT DOCUMENTS

| | | |
|---|---|---|
| 0060518B1 | 9/1982 | European Pat. Off. . |
| 0060518A1 | 9/1982 | European Pat. Off. . |
| 0123902A2 | 11/1984 | European Pat. Off. . |
| 0130520A1 | 1/1985 | European Pat. Off. . |
| 0164008A2 | 12/1985 | European Pat. Off. . |
| 0224210A1 | 6/1987 | European Pat. Off. . |
| WO 86/04610 | 8/1986 | PCT Int'l Appl. . |
| WO 86/05207 | 9/1986 | PCT Int'l Appl. . |
| 1560077 | 1/1980 | United Kingdom . |

OTHER PUBLICATIONS

Latt, et al., *Analytical Biochemistry*, 1972, vol. 50: pp. 56-62.

Josephy, et al., *Carcinogenesis*, 1982, vol. 3, No. 10, pp. 1227-1230.

Liem, et al., *Analytical Biochemistry*, 1979, vol. 98: pp. 388-393.

Josephy, et al., *Biochemical Pharmacology*, 1984, vol. 33, No. 7, pp. 1155-1156.

*Primary Examiner*—Michael G. Wityshyn
*Assistant Examiner*—Louise N. Leary
*Attorney, Agent, or Firm*—Shelley G. Precivale; Mark L. Bosse

[57] ABSTRACT

Methods and compositions are disclosed for determining a peroxidatively active substance (PAS). The methods comprise the step of detecting a fluorescent signal produced upon cleavage of a compound of the formula F-L-Q, wherein F is a fluorester capable of producing the signal, Q is a quencher capable of quenching the signal when linked to F, and L is a bond, or a linking group having a bond, wherein the bond is capable of being cleaved by a reaction of the PAS with a substrate of the PAS and a hydrogen donor wherein the cleavage of the bond substantially reduces the quenching. The methods have application in a wide variety of systems including assays and improved assays for analytes. Also disclosed are kits for conducting the methods and improvements in accordance with the present invention.

8 Claims, No Drawings

METHODS FOR DETERMINING PEROXIDATIVELY ACTIVE SUBSTANCES

BACKGROUND OF THE INVENTION

1. Field Of the Invention

The invention concerns methods and compositions for the determination of peroxidatively active substances, assays involving the methods of the present invention, and kits for conducting such methods and assays.

Exemplary peroxidatively active substances are peroxidase enzymes. The peroxidases are a group of enzymes which catalyze the oxidation of specific substrates by hydroperoxides usually hydrogen peroxide. Certain substrates (chromogenie substrates), when oxidized in this way, become strong chromophores, generating intense color. The peroxidases have been widely used as labels in assays, usually as conjugates with specific binding pair (SBP) members as assay components. The presence of such a labelled component can be readily detected by adding a solution comprising the specific chromogenic substrate and a peroxide.

One of the more widely used peroxidases is horse radish peroxidase (HRP), for which a specific substrate is tetramethylbenzidine (TMB). HRP has found broad application as a marker enzyme in enzyme-immunological determination methods (enzyme immunoassays, EIA). A common feature of EIA systems is the exploitation of specific binding pair member interaction, such as an antigen-antibody interaction, for the determination of the presence or concentration of an analyte, e.g. antigen or antibody. A multitude of EIA systems have been described. These may be classified, for example, as systems with enzyme-labelled antigen and as systems with enzyme-labelled antibody.

One example of an EIA system with labelled antigen is the competitive solid phase EIA (enzyme linked immunosorbant assay, ELISA). In this system a known amount of an enzyme-labelled antigen and the antigen to be determined (analyte) compete for the limited number of binding sites of a specific antibody, which is immobilized on a solid phase. The higher the concentration of analyte, the lower the amount of enzyme-labelled antigen bound to the immobilized antibody. Making use of a calibration curve, the determination of the enzyme activity bound to the solid phase by interaction with the antibody allows the determination of the analyte concentration.

Another example is a labelled-antibody EIA which is a sandwich "assay" (or two site enzyme immunometric test). The assay includes two immunological reactions. In the first reaction a macromolecular antigen is bound more or less completely to an antibody immobilized on a solid phase. Next, the bound antigen is reacted with an excess of a conjugate consisting of a specific antibody and enzyme. The extent of the binding of the labelled antibody is proportional to the amount of antigen; thus, the determination of the remaining enzyme activity after removal of excess conjugate is a measure of the amount of antigen.

Another example of an EIA is a homogeneous enzyme immunoassay sold by Syva Company, Palo Alto, California under the trade name EMIT. In EMIT assays the reaction takes place in one step in solution. Typically, the analyte from the test sample is combined with an enzyme-labelled analyte analog. Both the analyte and enzyme-labelled analyte analog are capable of competing for binding sites on an antibody for the analyte which is included in the reaction medium. By comparison with known standards, the enzyme activity that remains after the sample and other reagents are combined is a measure of the amount of analyte in the sample.

Thus, the determination of enzyme activity is an essential step in all EIAs. In general, enzyme activity is determined by well-known procedures. Typically changes of optical properties (absorption, fluorescence, luminescence, and the like) of an appropriate substrate effected by the enzymatic action is followed. Appropriate measuring instruments are used, and a linear proportionality between measuring signal and an amount of enzyme is advantageous.

Numerous substrates for peroxidases, particularly horseradish peroxidase, have been reported. Many are chromogenic substrates that involve oxidation of a leuco dye to its colored form. Typical of this type of substrate is tetramethyl- benzidine, 3,3-bis-(3-carboxypropoxy)benzidine, N-ethyl-3-aminocarbazol, guiacol, azo-bis-tetramethyl-benzimidazole sulfonic acid (ABTS), etc. In another group of dye substrates, the oxidized substrate forms a color by reacting with its own unoxidized form. Examples of such self-coupling substrates include p-hydroxyphenylpropionic acid, 4-chloronaphthol, and o-phenylenediamine.

A second class of substrates, called "developers" are oxidized to intermediates that condense with color-forming molecules, called "couplers" to form dyes Typical of this class of substrates are N-methylbenzothiazolone hydrazone and aminoantipyrene, either of which on oxidation can couple to electrophilic compounds such as aminobenzoic acid, diketones, phenols, etc.

The second class of substrates are of special interest because $HRP/H_2O_2$ catalyzes the condensation of two compounds. Ease of manipulation makes a dual substrate system attractive for various applications in EIA.

In certain applications a sensitive, precipitable, chromogenic substrate is used. One such substrate which has been recently published by a group at Kodak is precipitable and has the capability of detecting <50 pg/Ml of HRP in 30 minutes (D. J. Dannet, et al., (1973) *Arch Biochem Biophys.*, 156:759; P. E. Weller, et al. (1985) *Arch Biochem. Biophys.*, 243(2):633–643; European Patent 02527457; H. B. Dunford et al. (1986) Arch Biochem Biophys, 251 (2):536–542; U.S. Pat. No. 4,089,747).

Benzidine and 3,3'-dimethoxybenzidine have been shown to oxidatively couple with 4-substituted or unsubstituted 2-t-butylphenols where the substituent is methoxy or halide (Josephy, etal.; *Carcinogenesis* (1982) 3 (10):1227–1230; and *Biochem. Pharmacol.* (1984) 33 (7):1155–1156). In these reactions the substituent, or hydrogen when there was no substituent, was displaced by the nitrogen of an oxidized benzidine to form a merocyanine dye. However, there was no recognition of the use of this reaction for determination of peroxidase activity or hydrogen peroxide concentration or of its use in assays for analytes. Further, there was no recognition of the use of the condensation reaction for generating a detectable signal by cleaving a bond to a signal suppressing substituent as where the substrates are of the formula S-L-M, wherein S is a signal generating moiety whose signal is modulated by signal modulating moiety M when M is bound to S, and L is a bond, or a linking group having a bond, which is capable of being cleaved by the reaction of PAS with a substrate of PAS and a hydrogen donor.

Also related to this class of substrates are dye substrates such as p-hydroxy-and p-amino-, particularly p-dialkylamino-, anilines. Some dye substrates of this class, after oxidization, condense with couplers and undergo bond cleavage resulting in the release of a second dye molecule and a molecule capable of fluorescing. In these cases the coupler was a p-amino- or p-hydroxy-phenyl ether of a dye molecule, and the substrates were used to determine hydrogen peroxide concentrations. Examples of this type of substrate are disclosed in European patent specification, publication No. 0060518 B1 (EPO patent application 82101947.8). Again there was no recognition of whether or not these compounds were even useful for the determination of peroxidase activity; or of the use of the condensation reaction for generating a detectable signal by cleaving a bond to a signal suppressing substituent as where the substrates are of the formula S-L-M, wherein S is a signal generating moiety whose signal is modulated by signal modulating moiety M when M is bound to S, and L is a bond, or a linking group having a bond, which is capable of being cleaved by the reaction of PAS with a substrate of PAS and a hydrogen donor. On the other hand, the compositions of the present invention are useful for the determination of peroxidase activity and are comprised of a structural moiety that is capable of producing a signal and a structural moiety that modulates the signal produced by the signal producing moiety. An example of the present compositions are compounds comprised of a signal group capable of fluorescing linked to a signal modulating group capable of quenching the fluorescence of the signal group by energy transfer.

2. Description of the Related Art

European patent specification, publication No. 0060518 B1, as set forth above, discloses a reagent for assaying hydrogen peroxide and a method of quantitative assay for hydrogen peroxide.

Latt, S.A.; et al. in *Anal. Biochem.* (1972) 50 (1):56–62 disclose a fluorescence determination of carboxypeptidase A using a poly(amino acid) substrate analog having two fluorescent labels, one of which is quenched when bound to the substrate analog. Upon hydrolysis of the quenched label by carboxypeptidase A, its fluorescence is restored. The reaction is said to be useful for mechanistic research, assays for inhibition of cobalt carboxypeptidase by amino acids (e.g. L-phenylalanine) and assays for peptidase activity.

Josephy, al. in *Carcinoaenesis* (1982) 3 (10):1227–1230 discloses the chemical structures of adducts formed by the oxidation of benzidine in the presence of phenols. Josephy, et al. in *Biochem. Pharmacol.* (1984) 33 (7):1155–1156 discloses the reaction of 4-substituted phenols with benzidine in a peroxidase system.

U.S. Pat. No. 4,853,328 discloses a reagent for assaying hydrogen peroxide and a method of quantitative assay for hydrogen peroxide.

PCT International Application, Publication No. WO86/05207, discusses improvements relating to assay reagents, which are peroxidase-containing and tetramethylbenzidine peroxidase-substrate reagents.

European Patent Application 0123902 A2 discloses a procedure for the determination of peroxidase activity by end dilution titration and means for its realization. The procedure is carried out with a benzidine derivative in the presence of a non-chromogenic or low-chromogenic phenylene derivative, which is a proton donor, to retard color development for a sufficient period of time to permit a sharp dilution end point and thereafter detecting the peroxidase activity.

U.S. patent application No. 4,279,993 discloses an indicator composition and test device containing amine oxide and a method of its use. The composition contains a benzidine-type indicator.

Semi-quantitative determination of urine glucose with a carrier matrix containing glucose oxidase, a peroxidase and m-anisidine, optionally with tetramethylbenzidine is disclosed in U.S. Pat. No. 4,391,905 and 4,391,906.

U.S. Pat. No. 4,556,640 discusses a stabilized test composition, device and method for the determination of peroxidatively active substances.

Ionic compounds containing the cationic meriquinone of a benzidine are disclosed in U.S. Pat. No. 4,789,630.

European Patent Application, Publication No. 0060518 A1 discusses reagents for assay of hydrogen peroxide especially in diagnostic systems with a chemical moiety and fluorescing moiety present.

A test composition for peroxidatively active substance with aniline derivative present as a stabilizer and device and method for the determination of peroxidatively active substances is disclosed in European Patent Application, Publication No. 0130520 A1.

Ethanol determination in aqueous samples with alcohol oxidase, peroxidase, and a reduced chromogenic indicator is disclosed in European Patent Application, Publication No. 0164008 A2.

U.S. Pat. No. 4,587,220 discusses ascorbate interference-resistant composition, device and method for the determination of peroxidatively active substances.

Quantitative determination of hemoglobin and cytochemicals staining for peroxidase using 3,3'-5,5'-tetramethylbenzidine dihydrochloride as a safe substitute for benzidine is disclosed by H. H. Liem, et al. (1979) *Analytical Biochemistry* 98:388–393.

Europaische Patentanmeldung 0224210 A1 discloses a color forming reagent for measuring peroxidase activity containing tetralkylbenzidine, peroxide and acidic buffer to improve sensitivity.

Stabilized enzyme substrate solutions are disclosed in PCT International Application, Publication No. WO 86/04610.

U.S. Pat. No. 4,503,143 discloses an enzyme immunoassay with two-parts solution of tetramethylbenzidine as chromogen.

A test composition for the detection of peroxidatively active substances is disclosed in UK Patent Specification 1560077.

U.S. Pat. No. 3,527,331 discusses substantially anhydrous, solid assay materials for the determination of reagent for assaying aldolase. The materials are rendered storage stable by the presence of certain polyhydric compounds preferably mannitol, sorbitol, lactose or polyvinyl alcohol. An indicator composition and test device containing amine oxide and a method of its use is disclosed in U.S. Pat. No. 4,279,993.

U.S. Pat. No. 4,310,626 discloses interference-resistent composition, device and method for determining a peroxidatively active substance in a test sample.

Stabilization of indicators for detecting enzyme activity is disclosed in U.S. Pat. No. 4,615,972.

An assay for peroxidative enzyme activity is discussed in U.S. Pat. No. 4,596,770.

A specific binding assay employing an enzyme-cleavable substrate as a label is disclosed in U.S. Pat. No. 4,279,992.

An agent for the determination of peroxidase activity, with stabilizer, is disclosed in U.S. Pat. No. 4,891,314.

SUMMARY OF THE INVENTION

The present invention relates to methods, assays, kits, and compounds that are useful in a wide variety of systems including assays for analytes.

One aspect of the present invention involves a method (method A) for determining a peroxidatively active substance (PAS) which comprises the step of detecting a fluorescent signal produced upon cleavage of a compound of the formula F-L-Q, wherein F is a fluorescer capable of producing said signal, Q is a quencher capable of quenching said signal when linked to F, and L is a bond, or a linking group having a bond, wherein said bond is capable of being cleaved by a reaction of said PAS with a substrate of said PAS and a hydrogen donor wherein said cleavage of said bond substantially reduces said quenching.

Another aspect of the present invention relates to a method (method B) for determining a peroxidatively active substance (PAS), said method comprising the steps of (1) contacting a sample suspected of containing PAS with (a) a hydroperoxide; (b) a hydrogen donor; and (c) a compound of the formula F-L-Q wherein F is a fluorescer capable of producing a fluorescent signal, Q is a quencher capable of quenching by energy transfer said signal when linked to F, and L is a bond or linking group containing a bond wherein said bond is capable of being cleaved by a reaction of said PAS with a substrate of said PAS and a hydrogen donor wherein said cleavage substantially reduces said quenching; and (2) detecting said signal. Such a method is useful in a wide variety of systems including assays for analytes. Another aspect of the present invention is directed to the above method B wherein said F-L-Q is of the formula:

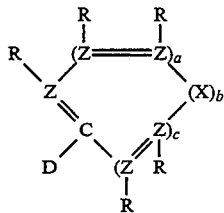

wherein:
X is O, S (sulfur atom), or $NR_1$ wherein $R_1$ is H, alkyl, or aryl, with the proviso that O or S (sulfur atom) be bound to carbon atoms;
Z is C or N;
b is 0 or 1;
a and c are independently 0, 1 or 2 with the proviso that the ring contain 5 to 7 atoms;
R is independently H or a substituent having from 1 to 50 atoms other than hydrogen, which atoms are independently selected from the group consisting of carbon, oxygen, nitrogen, sulfur, phosphorus, and halogen, or two R's can be taken together to form a ring, being substituted or unsubstituted, a single ring or part of a fused ring system, wherein one R is OH, SH (thio), or amino nitrogen bound to a site on the ring, wherein said site is separated from D by an even number of ring atoms excluding X; and
D is O or S (sulfur atom) wherein said O or S (sulfur atom) is bonded to F or Q with the proviso that the two electron oxidation potential of said compound of the formula F-L-Q is greater than that of said hydrogen donor.

Another aspect of the present invention is directed to the above method B wherein said hydrogen donor is of the formula:

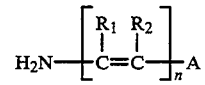

wherein:
A is a hydroxyl group, an amino group, $—NHR_3$, or $—NR_3R_4$, wherein $R_3$ and $R_4$ are independently an alkyl group having 1 to 5 carbon atoms, a cycloalkyl group having 3 to 6 carbon atoms, a hydroxyalkyl group having 1 to 5 carbon atoms, or an acylaminoalkyl group having 1 to 5 carbon atoms; or $R_3$ and $R_4$ may combine to form a ring which is unfused or fused, substituted or unsubstituted, a single ring, or part of a multi-ring system;
$R_1$ and $R_2$ are independently a hydrogen atom, an alkyl group having 1 to 5 carbon atoms, an alkoxy group having 1 to 5 carbon atoms, a halogen atom, a carboxyl group, a methanesulfonyl group or a phenyl group; or $R_1$ and $R_2$ may combine together to form a cycloalkene, an aromatic ring or a heterocyclic ring; and
n is 1 to 5.

Another aspect of the present invention involves an improved assay for an analyte, said assay comprising the step of combining a medium suspected of containing said analyte or an agent probative of said analyte with one or more members of a signal producing system, the improvement (improvement A) comprising the steps of (1) contacting a sample suspected of containing PAS with (a) a hydroperoxide; (b) a hydrogen donor; and (c) a compound of the formula F-L-Q wherein F is a fluorescer capable of producing a fluorescent signal, Q is a quencher capable of quenching by energy transfer said signal when linked to F, and L is a bond or linking group containing a bond wherein said bond is capable of being cleaved by a reaction of said PAS with a substrate of said PAS and a hydrogen donor wherein said cleavage substantially reduces said quenching; and (2) detecting said signal. Such an improvement is useful in a wide variety of systems including assays for analytes.

Another aspect of the present invention is directed to the above improvement A wherein said F-L-Q is of the formula:

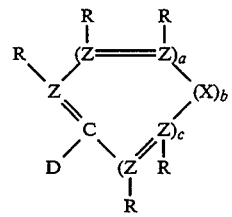

wherein:

X is O, S (sulfur atom), or $NR_1$ wherein $R_1$ is H, alkyl, or aryl, with the proviso that O or S (sulfur atom) be bound to carbon atoms;

Z is C or N;

b is 0 or 1;

a and c are independently 0, 1 or 2 with the proviso that the ring contain 5 to 7 atoms;

R is independently H or a substituent having from 1 to 50 atoms other than hydrogen, which atoms are independently selected from the group consisting of carbon, oxygen, nitrogen, sulfur, phosphorus, and halogen, or two R's can be taken together to form a ring, being substituted or unsubstituted, a single ring or part of a fused ring system, wherein one R is OH, SH (thio), or amino nitrogen bound to a site on the ring, wherein said site is separated from D by an even number of ring atoms excluding X; and D is O or S (sulfur atom) wherein said O or S (sulfur atom) is bonded to F or Q with the proviso that the two electron oxidation potential of said compound of the formula F-L-Q is greater than that of said hydrogen donor.

Another aspect of the present invention is directed to the above improvement A wherein said hydrogen donor is of the formula:

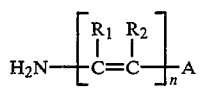

wherein:

A is a hydroxyl group, an amino group, —$NHR_3$, or —$NR_3R_4$, wherein $R_3$ and $R_4$ are independently an alkyl group having 1 to 5 carbon atoms, a cycloalkyl group having 3 to 6 carbon atoms, a hydroxyalkyl group having 1 to 5 carbon atoms, or an acylaminoalkyl group having 1 to 5 carbon atoms; or $R_3$ and $R_4$ may combine to form a ring which is unfused or fused, substituted or unsubstituted, a single ring, or part of a multi-ring system;

$R_1$ and $R_2$ are independently a hydrogen atom, an alkyl group having 1 to 5 carbon atoms, an alkoxy group having 1 to 5 carbon atoms, a halogen atom, a carboxyl group, a methanesulfonyl group or a phenyl group; or $R_1$ and $R_2$ may combine together to form a cycloalkene, an aromatic ring or a heterocyclic ring; and n is 1 to 5.

Another aspect of the present invention involves a kit (kit A) for detecting a peroxidatively active substance (PAS), said kit comprising in packaged combination a compound of the formula F-L-Q wherein F is a fluorescer capable of producing a fluorescent signal, Q is a quencher capable of quenching by energy transfer said signal when linked to F, and L is a bond or linking group containing a bond wherein said bond is capable of being cleaved by a reaction of said PAS with a substrate of said PAS and a hydrogen donor wherein said cleavage substantially reduces said quenching; and a hydrogen donor. Such a kit is useful for conveniently performing in a wide variety of systems including assays for analytes.

Another aspect of the present invention is directed to the above kit A wherein said F-L-Q is of the formula:

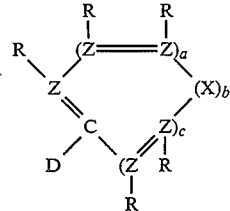

wherein:

X is O, S (sulfur atom), or NR, wherein $R_1$ is H, alkyl, or aryl, with the proviso that O or S (sulfur atom) be bound to carbon atoms;

Z is C or N;

b is 0 or 1;

a and c are independently 0, 1 or 2 with the proviso that the ring contain 5 to 7 atoms;

R is independently H or a substituent having from 1 to 50 atoms other than hydrogen, which atoms are independently selected from the group consisting of carbon, oxygen, nitrogen, sulfur, phosphorus, and halogen, or two R's can be taken together to form a ring, being substituted or unsubstituted, a single ring or part of a fused ring system, wherein one R is OH, SH (thio), or amino nitrogen bound to a site on the ring, wherein said site is separated from D by an even number of ring atoms excluding X; and D is O or S (sulfur atom) wherein said O or S (sulfur atom) is bonded to F or Q with the proviso that the two electron oxidation potential of said compound of the formula F-L-Q is greater than that of said hydrogen donor.

Another aspect of the present invention is directed to the above kit A wherein said hydrogen donor is of the formula:

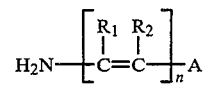

wherein:

A is a hydroxyl group, an amino group, —$NHR_3$, or —$NR_3R_4$, wherein $R_3$ and $R_4$ are independently an alkyl group having 1 to 5 carbon atoms, a cycloalkyl group having 3 to 6 carbon atoms, a hydroxyalkyl group having 1 to 5 carbon atoms, or an acylaminoalkyl group having 1 to 5 carbon atoms; or $R_3$ and $R_4$ may combine to form a ring which is unfused or fused, substituted or unsubstituted, a single ring, or part of a multi-ring system;

$R_1$ and $R_2$ are independently a hydrogen atom, an alkyl group having 1 to 5 carbon atoms, an alkoxy group having 1 to 5 carbon atoms, a halogen atom, a carboxyl group, a methanesulfonyl group or a phenyl group; or $R_1$ and $R_2$ may combine together to form a cycloalkene, an aromatic ring or a heterocyclic ring; and n is 1 to 5.

Another aspect of the present invention relates to a compound (compound A) of the formula F-L-Q wherein F is a fluorescer capable of producing a fluorescent signal, Q is a quencher capable of quenching said signal when linked to F, and L is a bond or linking group containing a bond wherein said bond is capable of being cleaved by a reaction of a peroxidatively active substance (PAS) with a substrate of said PAS and a hydrogen donor wherein said cleavage of said bond substantially reduces said quenching.

Another aspect of the present invention is directed to the above compound A wherein said F-L-Q is of the formula:

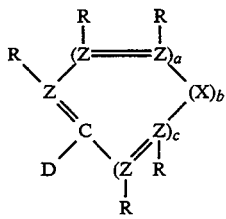

wherein:

X is O, S (sulfur atom), or $NR_1$ wherein $R_1$ is H, alkyl, or aryl, with the proviso that O or S (sulfur atom) be bound to carbon atoms;

Z is C or N;

b is 0 or 1;

a and c are independently 0, 1 or 2 with the proviso that the ring contain 5 to 7 atoms;

R is independently H or a substituent having from 1 to 50 atoms other than hydrogen, which atoms are independently selected from the group consisting of carbon, oxygen, nitrogen, sulfur, phosphorus, and halogen, or two R's can be taken together to form a ring, being substituted or unsubstituted, a single ring or part of a fused ring system, wherein one R is OH, SH (thio), or amino nitrogen bound to a site on the ring, wherein said site is separated from D by an even number of ring atoms excluding X; and D is O or S (sulfur atom) wherein said O or S (sulfur atom) is bonded to F or Q with the proviso that the two electron oxidation potential of said compound of the formula F-L-Q is greater than that of said hydrogen donor.

Another aspect of the present invention is directed to the above compound A wherein said hydrogen donor is of the formula:

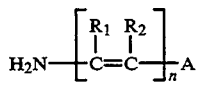

wherein:

A is a hydroxyl group, an amino group, $-NHR_3$, or $-NR_3R_4$, wherein $R_3$ and $R_4$ are independently an alkyl group having 1 to 5 carbon atoms, a cycloalkyl group having 3 to 6 carbon atoms, a hydroxyalkyl group having 1 to 5 carbon atoms, or an acylaminoalkyl group having 1 to 5 carbon atoms; or $R_3$ and $R_4$ may combine to form a ring which is unfused or fused, substituted or unsubstituted, a single ring, or part of a multi-ring system;

$R_1$ and $R_2$ are independently a hydrogen atom, an alkyl group having 1 to 5 carbon atoms, an alkoxy group having 1 to 5 carbon atoms, a halogen atom, a carboxyl group, a methanesulfonyl group or a phenyl group; or $R_1$ and $R_2$ may combine together to form a cycloalkene, an aromatic ring or a heterocyclic ring; and n is 1 to 5.

DESCRIPTION OF THE SPECIFIC EMBODIMENTS

The present invention is directed to the detection of a peroxidatively active substance such as a peroxidase. In the method of the invention a sample is contacted with (a) a hydroperoxide, (b) a hydrogen donor, and (c) a compound of the formula S-L-M, wherein S is a signal generating moiety whose signal is modulated by signal modulating moiety M when M is bound to S, and L is a bond, or a linking group having a bond, which is capable of being cleaved by the reaction of PAS with a substrate of PAS and a hydrogen donor, wherein cleavage of said bond substantially reduces the modulation of the signal from S by M, and wherein the compound of the formula S-L-M has a two electron oxidation potential greater than that of the hydrogen donor. The product of the reaction of the above reaction is detected by measurement of a signal, including without limitation absorbance, fluorescence, chemiluminescence, potentiometric, turbidimetric, etc. Generally, the hydrogen donor will be a benzidine where at least one amine nitrogen of the benzidine is primary (having 2 hydrogens attached) and at least one of the positions on the aromatic ring ortho to that particular amine group bears a hydrogen atom substituent. Except for the above requirements for benzidine, the benzidine may be unsubstituted or substituted in other positions with the proviso that substantial planarity of the benzidine system must be maintained to allow oxidation to occur and the oxidation potential must be sufficiently low to permit oxidation by the hydroperoxide. The compound of the formula S-L-M may be any compound which will enter into a cleavage reaction with the oxidized form of the hydrogen donor to yield a detectable product wherein the modulation of the signal from S by M has been substantially reduced as a result of the cleavage reaction.

The present invention is based on the observation that certain hydrogen donors oxidized with a peroxidatively active substance, such as a peroxidase (e.g. horseradish peroxidase), and a hydroperoxide enter into cleavage reactions with certain compounds of the formula S-L-M. Such compounds are generally phenols and anilines that are para-substituted with leaving groups which contain a signal generating or signal modulating group and are further substituted so as to be capable of modulating the signal if the leaving group is a signal generator or to generate a signal if the leaving group is a signal modulator. When cleavage takes place, the modulation of the signal (e.g. fluorescence) from S by the action of M (e.g. quenching) is substantially reduced. The sensitivity enhancement achieved in the present invention is greater than the sensitivity achieved in other systems such as N,N-dimethylphenylenediamine with gentisic acid.

The present invention provides a method for very rapid catalytic cleavage of otherwise very stable bonds with the formation of a detectable product. The method permits detection of peroxidatively active catalysts, such as peroxidases, with very great sensitivity by means of a class of substrates that incorporate a signal producing label (e.g. a fluorescent label) that is modulated (e.g. quenched) by an incorporated modulator (e.g. quencher) and yet which, when desired, can yield products capable of generating a signal (e.g. fluorescence). These products can, for example, be caused to generate a signal at a site where a peroxidase is localized as a result of the binding reaction in an immunoassay and thus provide a means for highly sensitive detection of antigenic analytes alternatively, they can be caused to generate a signal in a homogenous system such as a homogenous immunoassay for an analyte. Additionally, the invention provides a way to release covalently bound groups for other purposes under very mild conditions such as the release of a fluorogenic, chromogenic or chemiluminescent group.

In the present invention hydrogen donors (as defined) are oxidized with a peroxidase and a hydroperoxide in the presence of a compound of the formula S-L-M, wherein S is a signal generating moiety whose signal is modulated by signal modulating moiety M when M is bound to S, and L is a bond, or a linking group having a bond, which is capable of being cleaved by the reaction of PAS with a substrate of PAS and a hydrogen donor, wherein cleavage of said bond substantially reduces the modulation of the signal from S by M. The oxidized hydrogen donor then reacts with the compound of the formula S-L-M such that a cleavage reaction takes place wherein S is separated from M. The hydrogen donor will generally be bound in whole or in part to one or the other of the groups S and M after the cleavage reaction. Additionally, the group L, when not a bond, may be in whole or in part bound to one or the other of the groups S and M after the cleavage reaction. The term "in whole or in part" comprehends that parts of the hydrogen donor and the group L, when not a bond, may not be bound to either of the groups S and M after the cleavage reaction and may instead appear among the reaction products as separate products.

A water solubilizing or insolubizing groups when present, may be bound to the hydrogen donor or the groups S, L, or M. One or more of the reaction products are capable of generating a signal and each of the products can be manipulated to be soluble or insoluble depending on the substituents of the hydrogen donor and/or the compound of the formula S-L-M. Exemplary of water-solubility imparting functionalities are sulfate, sulfite, phosphate, phosphite, and so forth. Exemplary of water insolubility imparting groups are hydrophobic groups such as alkyl, acyl, etc.

For example, if the hydrogen donor becomes bound to the signal modulating group M during the cleavage reaction, then to obtain a more precipitable signal modulating product oppositely charged species for the hydrogen donor and the signal modulating group M can be chosen. After reaction, a cleavage product comprising the signal generating group M bound to the hydrogen donor can form having all charges neutralized. The precipitation of this product is thus enhanced. For example, the substituents in the 3 and 3'-positions of a benzidine hydrogen donor can contain negative charges and a substituent of the signal modulating group M can contain a corresponding number of positive charges. A resulting cleavage product is neutral.

Alternately, regardless of which of the groups S and M are bound to the hydrogen donor after cleavage the hydrogen donor may have no charged substituents, the signal generating groups may have a hydrophobic substituent that would render it insoluble but for the presence of a charged substituent on the signal modulating group M. On cleavage, the resulting signal generating hydrophobic product is no longer soluble.

Before proceeding further with the description of the specific embodiments of the present invention, a number of terms will be defined.

Oxidation of a hydrogen donor—refers to the abstraction of two electrons and one or two protons, from a hydrogen donor, typically a benzidine. The oxidation normally is produced by a hydroperoxide oxidant but could, for example, be produced by electrochemically oxidizing the peroxidatively active substance. The oxidant is usually hydrogen peroxide, perborate, or an alkyl or acylhydroperoxide. Hydrogen peroxide can be added as a reagent or can be generated in situ, by, for example, reaction of glucose and oxygen with glucose oxidase. The product, when the hydrogen donor is a benzidine, is a benzidine quinone imine which may be electrically neutral or be singly or doubly protonated depending on the acidity of the medium.

Two electron oxidation potential—is based on the ability of the compound of the formula S-L-M to give up two electrons and lose zero to two protons depending on the acidity of the medium. The two electron oxidation potential can be determined in a standard electrochemical cell using a reference electrode such as a hydrogen, calomel, or Ag/AgCl electrode usually using a dropping mercury working electrode. The pH of the solution of compound of the formula S-L-M and benzidine will be adjusted prior to measurement to the same value as used in the desired cleavage reaction. Alternatively, it can be observed directly whether the benzidine quinoneimine can be reduced to benzidine by the compound of the formula S-L-M by combining the two compounds in a solution and observing the disappearance of color of the quinoneimine and reappearance of benzidine which may be detected spectroscopically or by chromatography.

As mentioned above, the compound of the formula S-L-M should not be able to reduce the oxidized benzidine to benzidine. The oxidation potential of the compound must be carefully selected to match the benzidine that is being used.

Hydroperoxide—an oxidant, refers to any compound capable of participating in the oxidation of the hydrogen donor by means of the peroxidatively active substance which contains the hydroperoxide (—O—O—H) group. Examples of such hydroperoxides include both organic and inorganic hydroperoxides, e.g., hydrogen peroxide, urea hydrogen peroxide, peracids, and perborate.

Organic hydroperoxides contemplated for use in the invention can be selected from many well known organic hydroperoxides. Among hydroperoxides which are particularly suitable are methyl hydroperoxide, ethylhydroperoxide, cumeme hydroperoxide, t-butyl hydroperoxide, diisopropylbenzene hydroperoxide, 2,5-dimethylhexane-2,5- dihydroperoxide, paramenthane hydroperoxide, and other well-known hydroperoxides, which are suitable for oxidizing the hydrogen donor used, or mixtures of these compounds.

Peroxidatively active substance (PAS)—refers to an oxidation catalyst which catalyzes reduction of a hydroperoxide by an electron donating agent, particularly a benzidine. Subclasses of peroxidative catalysts include aquated or otherwise complexed transition metal ions which are reactive toward electron transfer (e.g., copper, iron, cobalt, manganese), hemes, hemoproteins, and specific enzymes known as peroxidases such as lactoperoxidase. A subclass of peroxidases, the "haloperoxidases", employ halide ion as a cofactor. The most commonly used peroxidase is purified from horseradish roots and is designated horseradish peroxidase or HRP.

Benzidine—a 4,4'-diaminobiphenyl; for purposes of the present invention at least one of the amino groups of the benzidine is primary and at least one position on the aromatic ring ortho to such amino group bears a hydrogen atom substituent. To exemplify this distinction benzidine and 3,3'-dimethylbenzidine function in the present invention, whereas 3,3',5 5'-tetramethylbenzidine and N,N,N',N'-tetramethylbenzidine do not react at a rate acceptable for assays. The remaining positions on the amino groups of the benzidine may contain substantially electroneutral substituents such as aryl, alkyl, H, or alkoxy, but not carbonyl, sulfonate or other electron withdrawing groups, that is, anything that causes too large an increase in the oxidation potential and inactivates the benzidine to oxidation. The remaining positions on the aromatic ring may include in addition weakly electron withdrawing groups such as halogen, acylamido, phosphates, etc, again the primary requirement that the oxidation of the benzidine not be inhibited. Further, the additional substituents may contain additional ring systems, as long as substantial planarity of the molecule is maintained so that oxidation of the benzidine in accordance with the present invention may be achieved.

In one aspect the benzidine has the formula—

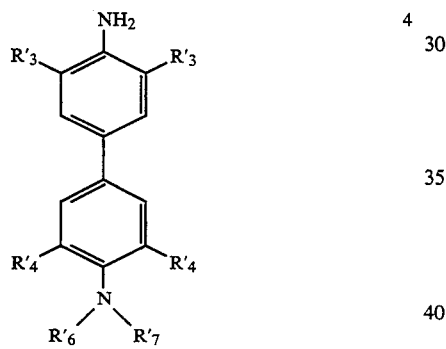

4 wherein:
R'$_6$, and R'$_7$ are independently selected from the group consisting of H, alkyl, alkoxy, aryl, and aralkyl wherein carbon atoms of a member of said group bear H or one or more of the functionalities selected from the group consisting of ethers, olefins, acetylenes, thioethers, amines, carboxylic acids, sulfonic acids, phosphoric acids, ketones, aldehydes, nitriles, carboxamides, sulfonamides, carbamates and ureas, and R'$_3$ and R'$_4$ are a member independently selected from the group consisting of H, F, el, Br, I, arylthio, alkylthio, aryloxy, alkyl, alkoxy, aryl, aralkyl, and arylalkoxy wherein at least one of R'$_3$ is H and carbon atoms of a member of said group bear H or one or more of the functionalities selected from the group consisting of ethers, olefins, acetylenes, thioethers, amines, carboxylic acids, sulfonic acids, phosphoric acids, ketones, aldehydes, nitriles, carboxamides, sulfonamides, carbamates and ureas, where R'$_6$ and R'$_7$ may be taken together with R'$_3$ or R'$_4$, or R$_6$ may be taken together with R'$_7$, to form one or more rings that are fused (e.g., naphthyl, anthracyl, etc.), or unfused (e.g., biphenyl, etc.), saturated (e.g., aromatic or aryl), or unsaturated (e.g., cycloalkyl, etc.), or a combination thereof (e.g., cycloalkyl containing one or more olefin bonds).

In another aspect the benzidine has the formula—

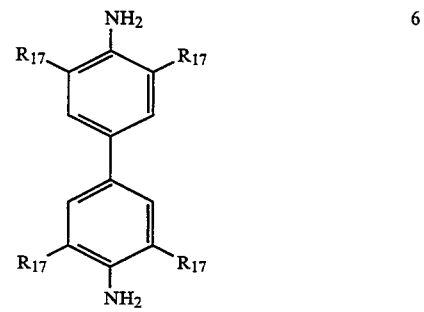

6 wherein R$_{17}$ is independently H, lower alkyl, lower alkoxy, or carboxy lower alkoxy, and at least one R$_{17}$ is H.

Exemplary benzidines are

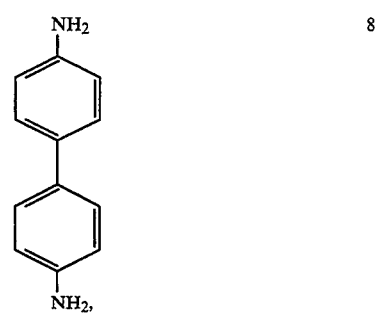

8

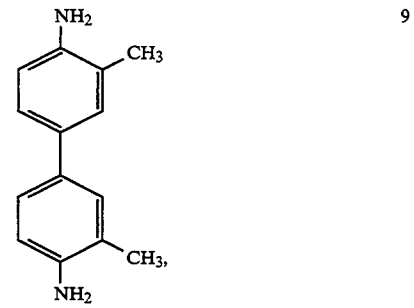

9

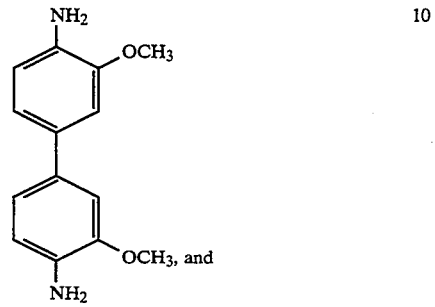

10

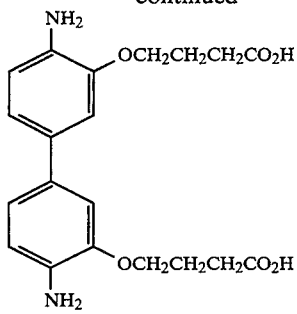

Benzidines that can be utilized in the present invention are generally known, commercially available or can be synthesized according to procedures well known to those skilled in the art.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylene—a divalent branched or unbranched radical derived from an aliphatic hydrocarbon by removal of one H atom; includes both lower alkylene (1–5 carbon atoms) and upper alkylene than 6 carbon atoms, usually 6 to 20 carbon atoms.

Carboxyalkyl—an alkyl group containing one (or more) carboxylic acid groups in place of one (or more) hydrogen atoms.

Carboxyalkylene—an alkylene group containing one (or more) carboxylic acid groups in place of one (or more) hydrogen atoms.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc.

Arylalkoxy—an aralkyl radical attached to the remainder of a molecule by an oxygen atom, e.g., benzoxy, 1-naphthylethoxy, etc.

Fused ring—a polycyclic compound in which at least two rings have two atoms in common, e.g., naphthalene, anthracene, etc.

Unfused (or single ring)—a compound having one or more rings none of which have two atoms in common, e.g., benzene, biphenyl, etc.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbons, oxygen, nitrogen, sulfur, and phosphorus.

Alkylthio—an alkyl radical attached to the remainder of a molecule by a sulfur atom, e.g., methylthio, ethylthio, etc.

Arylthio—an aryl radical attached to the remainder of a molecule by a sulfur atom, e.g., phenylthio, naphthylthio, etc.

Halogen—an atom selected from the group consisting of F, Cl, Br, and I, preferably from the group Cl, Br, and I.

Moiety—a structural subunit within a larger composition. For example, methylbenzene contains methyl and phenyl moieties, and ethyl chloride contains halo (in this case chloro), ethyl, methyl and methylene moieties. It is possible that a given subunit can be described as containing a single or a number of moietoes.

Electron—withdrawing group—a substituent which when bound to a molecule is capable of polarizing the molecule such that the electron-withdrawing group becomes electron rich and negatively charged. Such a group is electron attracting and may be, by way of illustration and not limitation, halogen (Cl, Br, I, F), $NO_2$, CN, $CONR''_2$, $NR'''$, $COOR''$, $-SO_3R''$, $-SO_2R''$, $-PO_3R''_2$, $-COR''$ wherein $R''$ is hydrogen, alkyl, or aryl, and the like.

Quinoid compound—paraquinoid; the chromophoric group

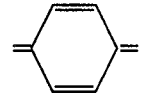

A substituent having from 1 to 50 atoms (other than the requisite hydrogen atoms necessary to satisfy the valencies of such atoms), which atoms are independently selected from the group consisting of carbon, oxygen, nitrogen, sulfur, halogen, and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), halogen (Cl, Br, I, F) wherein the O, N, S, Cl, Br, I, F or P, if present, are normally bound to at least a carbon atom and may be bound to one or more of each other or to hydrogen to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like. Illustrative of such organic radicals or groups, by way of illustration and not limitation, are alkyl, aryl, aralkyl, and alkyl, aryl, and aralkyl substituted with one or more of the aforementioned functionalities. It is contemplated within the scope of the present invention that such organic radicals can include signal generating group(s), generally fluorescent groups (F), and signal modulating groups (M), generally fluorescence quenching groups (Q).

Leaving group—a substituent on the compound of the formula S-L-M that is capable of being cleaved therefrom during the reaction of the compound with an oxidized hydrogen donor, generally a benzidine.

The leaving group of the present invention will include at least one signal generating group or signal modulating group but not both signal generating and signal modulating groups.

Compound of the formula S-L-M—the present invention relates to a compound of the formula S-L-M, wherein S is a signal generating moiety whose signal is modulated by signal modulating moiety M when M is bound to S, and L is a bond, or a linking group having a bond, which is capable of being cleaved by the reaction of PAS with a substrate of PAS and a hydrogen donor, wherein cleavage of said bond substantially reduces the modulation of the signal from S by M. Preferably, the compound of the formula S-L-M will be a compound of the formula F-L-Q wherein F is a fluorescer whose fluorescence is quenched by quencher Q by means of energy transfer, and L is a bond or linking group containing a bond wherein said bond is capable of being cleaved by the reaction of PAS with a substrate of said PAS and a hydrogen donor wherein cleavage of said bond substantially reduces the quenching of F by Q.

The compounds of the formula S-L-M or F-L-Q will be able to yield a detectible signal upon a cleavage reaction with an oxidized hydrogen donor in accordance with the present invention. The signal may be, for example, fluorescence, or chemiluminescence. Preferably, the signal will be fluorescence and the compound of the formula S-L-M will be a compound of the formula F-L-Q. Such a fluorescence signal can be produced by excitation of a signal group F such as a coumarin, xanthene, squaraine, or umbelliferone, fluorescein, bimane, merocyanine, naphthylamine, cyanine, luminol, acridinium ester, or luciferin oxalate ester group, and so forth.

The compounds of the formula S-L-M or F-L-Q will contain an aromatic or heteroaromatic group capable of reacting with an oxidized hydrogen donor, generally a benzidine. Such compounds will have 1 to 5 fused rings wherein a leaving group is bound to an aromatic or heteroaromatic ring having 5 to 7 atoms, the aromatic ring containing the leaving group will also contain a hydroxyl, sulfhydryl or amino group bound in a position separated by an even number of ring atoms from the leaving group such that the compound will have the ability to yield a detectable signal upon cleavage reaction in accordance with the present invention. Preferably, the aromatic ring will be a six-membered all-carbon aromatic ring wherein the leaving group is bound in a position para to the OH, SH (thio), or amino nitrogen (including amino nitrogen atom wherein the amino group is part of a second ring, i.e. ring amino nitrogen atoms). Compounds satisfying the above criteria can be employed as the compounds of the formula S-L-M or F-L-Q will contain in the present invention. Generally, the compound has a two electron oxidation potential greater than the benzidine; that is, it is unable to reduce oxidized hydrogen donor (e.g. an oxidized benzidine) to the hydrogen donor (e.g. the benzidine).

In accordance with the description of the compound S-L-M, the signal group S can be any group capable of generating a detectable signal wherein that signal is modulated by the modulating group M if S is bound to M by the linker L but is not modulated by M if S is not bound to M by the linker L. It is intended that this indicates that S generates a signal even when bound to M by the linker L but that the signal so generated is significantly modulated by M. Significant modulation is modulation sufficient to allow differentiation of bound S from unbound S under the conditions of and to the degree required of the application contemplated, generally an assay for an analyte.

Such signal groups include modulatable fluorescers, chemiluminscers, and the like. A particularly preferred class of signal groups are the fluorescent signal groups F. Such groups are fluorescers that are quenched by the modulating group M when that group is a fluorescence quenching group Q. Such fluorescent signal groups include fluorester organic groups such as coumarins, xanthenes, squaraines, umbelliferones, fluoresceins, bimanes, merocyanines, naphthylamines, cyanines, luminols, acridinium esters, luciferin oxalate esters, all of which may also contain one or more of the aforementioned substituents having from 1 to 50 atoms.

The fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their synthesis and use. The term fluorester is intended to include substances that emit light upon activation by electromagnetic radiation and includes fluorescent and phosphorescent substances, as well as scintillatots. The term chemiluminescer is intended to include substances that emit light upon chemical activation.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes, imines, anthracenes, oxacarbocyanine, merocyanine, 3-amino-equilenin, perylene, bis-benzoxazole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Individual fluorescent groups which have functionalities for binding to the linker L or can be modified to incorporate such functionalities include dansyl chloride, fluoresceins such as 3,6-dihydroxy-9-phenylxanthydrone, rhodamieisothiocyanate, N-phenyl 1-amino-8-sulfonatonaphthalene, N-phenyl 2-amino-6sulfonatonaphthalene, 4-acetamido-4'-isothiocyanatostilbene-2,2'-disulfonic acid, pyrene-3sulfonic acid, 2-toluidinonaphthalene-6-sulfonate, N-phenyl, N-methyl 2-amino-naphthalene-6-sulfonate, ethidium bromide, atebrine, automine-0, 2-(9'-anthroyl)palmitate, dansyl phosphatidyl-ethanolamine, N-(p-2-benzimidazolyl)-phenyl)maleimide, 4-phenyl-spiro(furan-2.1'-phthalan)-3-3'-dione, N,N-dioctadecyl oxacarbocyanine, N,N'-dihexyl oxa-carbocyanine, merocyanine, 4-(3'-pyrenyl)-butyrate, d-3-aminodesoxyequilenin, 12-(9'-anthroyl)-stearate, 2-methylanthracene, 9-vinylanthracene, 2,2'-vinylene-p-phenylene)bis-benzoxazole, p-bis[2-(4-methyl-5-phenyl-oxazolyl)]benzene, 6-dimethylamino-1,2-benzophenazin, retinol, bis(3'-aminopyridinium) 1,10-decandiyl diiodide, sulfonapthyl hydrazone of hellebrigenin, chlor-tetracylcline, N(7-dimethylamino-4-methyl-2-oxo-3-chromenyl)maleimide, N-[p-2benzimidazoyl-maleimide, N-(4fluoranthyl)maleimide, bis(-homovanilic acid), resazurin, 4-chloro-7-nitro-2.1.3-benzooxadiazole, merocyanine 540, resorufin, rose bengal, 2,3-diphenyl-3-(2H)-furanone, methylumbelliferone, 9,10-dibromoanthroacene, 9,10-diethinylanthracene, and eosin.

Another group of suitable fluorescent signal groups are described in detail in U.S. Pat. No. 4,318,846, the relevant disclosure of which, particularly, but no exclusively, columns 3–10, are incorporated herein by reference.

An alternative signal group S is a chemiluminescent source. The chemiluminescent source involves a group which becomes electronically excited by a chemical reaction and may then emit light which serves as the detectible signal or donates energy to a fluorescent acceptor.

The chemiluminescent source may have a single component or a plurality of components, usually two or three components. While it is feasible that there be a single molecule which is thermally labile and on decomposition chemiluminesces, such as certain dioxetanes, for a number of reasons the use of these molecules will not be commercially practical. While one could prepare reagents and maintain them at sufficiently low temperatures, so that the rate of decomposition was acceptably slow and then warm the reagent immediately prior to use, such technique will generally be inconvenient, even though it does have some parallel with radioimmunoassay. Therefore, for the most part, the chemiluminescence source will have at least two components and the major portion of the discussion will be directed to this situation. The chemiluminescent source may be divided into two categories: those which do not involve the intermediacy of enzyme catalysis; and those which do involve enzyme catalysis.

Considering chemiluminescent sources which do not involve enzyme catalysis, only those sources can be employed which chemiluminesce under conditions which do not interfere with the other reactions or interactions involved in the assay. While ordinarily, chemiluminescent sources which are dependent on nonaqueous solvents and strong basic conditions, greater than pH11, will not be useful, techniques can be employed involving rapid injections or flow techniques where the modulated emission is substantially completed before the protein is denatured and significant dissociation occurs. After injection of base, one would observe a burst of light, which could be measured.

A diverse number of families of source have been found to provide chemiluminesce under a variety of conditions. One such family are the 2,3-dihydro-1,4-phthalazinediones. The most popular of these sources is luminol, which is the 5-amino member. Other members of the family include the 5-amino-6,7,8-trimethoxy and the dimethylamino[ca]benz analog. These sources can be made to luminesce with alkaline hydrogen peroxide or calcium hypochlorite and base. Another family of sources is the 2,4,5-triphenylimidazoles, with lophine as the common name for the parent. Chemiluminscent analogs include paradimethylamino and methoxy substituents.

The next source are the indolen-3-yl hydroperoxides, precursors thereto and derivatives thereof.

The next source is the bis-9,9'-biacridium salts, of which lucigenin, N,N'a-dimethyl-9,9'-biacridinium dinitrateis illustrative. These materials chemiluminesce upon combination with alkaline hydrogen peroxide.

The next source is acridinium salts which are substituted in the 9 position. Particular substituents are carboxylic esters, particularly the aryl esters, acyl substituents, particularly benzoyl, and cyano. Alkaline hydrogen peroxide is employed to induce chemiluminescence.

Another source is various acyl peroxy esters and hydroperoxides, which may be formed in situ, in combination with compounds such as 9,10-diphenylanthracene.

Another source is various acyl peroxy esters and hydroperoxides, which may be formed in situ, in combination with compounds such as 9,10-diphenylanthracene.

Another source is hydroperoxides, e.g. tetralin hydroperixide, in combination with metal complexes, particularly porphyrins and phthalocyanines, where the metals are iron and zinc.

Preferred systems are those which provide a satisfactory quantum efficiency of emission from the chemiluminescer at a pH at or below 11, preferably at or below 10.

The next source is based on chemiluminescers which chemiluminesce under enzymatic catalysis. Primarily, there are two groups of enzymatically catalyzed chemiluminescers. The first group is those sources which chemiluminesce in combination with alkaline hydrogen peroxide. By employing a peroxidase e.g. horse radish peroxidase, in combination with hydrogen peroxide and the chemiluminescer, chemiluminescence can be achieved. Illustrative systems include 2,3-dihydro-1,4-hthalazinediones.

The second enzymatic source of chemiluminescence is based on luciferins and their analogs and luciferases. Of particular importance are bacterial luciferases.

Each of these compounds can be appropriately modified by standard synthetic techniques for incorporation as the signal group S. It should be noted that the absorption and emission characteristics of the bound signal groups may differ from the unbound groups.

When referring to the various wavelength ranges and characteristics of the signal groups, it is intended to indicate the signal groups characteristic in the form and under the condition in which the signal is detected.

In accordance with the description of the compound S-L-M, the modulating group M can be any group capable of modulating the detectable signal generated by the signal group S if M is bound to S by the linker L but which does not modulate the signal under the conditions of its detection when M is not bound to S. It is intended that this indicates that S is capable of generating a signal when bound to M by L but that such a signal is modulated by M such that, in relationship to the signal when not bound, it is significantly reduced in intensity or duration, shifted to a different wavelength, or delayed or accelerated in time sequence relative to the activation means.

The modulating group M when the signal group S is a fluorescer or chemiluminescer is a chromophore which absorbs light in the wavelength band emitted by the fluorester or chemiluminscer. For simplicity such groups will be referred to together as quenchers. Preferably, the quencher will absorb light at a wavelength close to the emission maximum wavelength of the fluorescer or chemiluminescer. What is desired, is that there be a high efficiency of energy transfer when the quencher is in relatively close juxtaposition to the fluorescer or source. Normally, the quencher will absorb light at greater than about 350Å, more usually at greater than about 400Å. Various chromophores which may be employed as quenchers include the xanthene dyes, which include the fluoresceins derived from 3,6-dihydroxy-9-phenylxanthhydrol and rosamines and rhodamines, derived from 3,6-diamino-9-phenylxanthhydrol. The rhodamines and fluoresceins have a 9-o-carboxyphenyl group and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Other dyes which may be used as quenchers include 3-phenyl-7-isocyanatocoumarin, acridines, such as 9-isothiocyanatoacridine and acridine orange; N-(p-(2-benzoxazolyl)phenyl)maleimide; benzoxadiazoles, such as 4-chloro-7-nitrobenzo-2-oxa-1,3-diazole and 7-(p-methoxybenzylamino)-4-nitrobenzo -2-oxa-1,3-diazole; stilbenes, such as 4-dimethylamino-4'-isothiocyanatostilbene and 4-dimethylamino-4'-maleimidostilbene N,N'-dioctadecyloxacarbocyanine p-toluenesulfonate; pyrenes, such as 8-hydroxy-1,3,6-pyrenetrisulfonic acid, and 1-pyrenebutyric acid; merocyanines e.g merocyanine 540, rose bengal, 2,4-diphenyl-3(2H)-furanone; cyanines, anthiaquinones; porphyrines; triarylmethanes; as well as other readily available dyes which are capable of quenching. These dyes, either have active functionalities for conjugation or such functionalities may be readily introduced.

It should further be noted that the absorption and emission characteristics of the dye may vary from being free in solution and being bound to a protein or ligand. Therefore, when referring to the various wavelength ranges and characteristics of the dyes, it is intended to indicate the dyes as employed and not the dye which is unconjugated and characterized in an arbitrary solvent. In the area of overlap between the chemiluminescer and quencher, it is desirable that the quencher should have a high transition probability.

Finally, the "blue fluorescent proteins" and/or "green fluorescent proteins" normally associated with certain bacterial luciferases e.g. the luciferase from Photobacterium fisheri, may also be used as a quencher.

Preferably, the compound will be of the formula F-L-Q and the modulating group will be a fluorescence quencher.

Suitable combinations (F/Q) of fluorescer (F) and quencher (Q) groups include by way of example and not limitation naphthalene/anthracene, α-naphthylamine/-dansyl, tryptophan/dansyl, dansyl/fluorescein, fluorescein/ritodamine, tryptophan/fluorescein, BPM/thiochrome BPM/ANS, thiochrome/DDPM, and ANS/DDPM. Suitable combinations (C/M) of chemiluminescer (C) and modulator (M) groups include by way of example and not limitation luminol/fluorescein, luminol/eosin, luminol/rhodamine S, DBPD/9,10-diphenyl anthralene, DBD/N-methylacridone, DBD/carbazole, DBD/2,3-denzocarbazole, DBD/3,4-benzocarbazole. Chemical structures and supportive references for each of the above fluorescer/quencher and chemiluminescer/modulator combinations can be found in U.S. Pat. No. 4,318,981. The relevant disclosure of which, particularly, but not exclusively, columns 5-10, are incorporated herein by reference.

The group of suitable fluorescers described in and incorporated by reference above from U.S. Pat. No. 4,318,846 can, when appropriately substituted as described, function as well as suitable quenchers.

In accordance with the description of the compound S-L-M, the group L can be a bond or linking group capable of being cleaned by reaction with the oxidized hydrogen donor. Generally, the group L will be contained in a functional group such as an ether, thioether, ester, amide, or carbonate group.

It is intended that if L is a bond, then the structural requirements, set forth above, for the compound of the formula S-L-M will be satisfied by the modulator group M when the leaving group compresses a signal group S, or by the signal group S when the leaving group comprises a modulation group M.

Specifically, if L is a bond, then S (when the leaving group comprises M) or M (when the leaving group comprises S) will be comprised of an aromatic or heteroaromatic ring having 5 to 7 atoms (optionally having 1 to 5 fused rings) wherein a leaving group is bound in a position separated by an even number of ring atoms (e.g. ortho or para in a six-membered aromatic ring) from an OH, SH (thio) or amino nitrogen (including ring amino nitrogens) - of course S or M in such a case can be further substituted as described herein.

Generally, L is selected so that S and M are spaced to optimize the modulation of S by M. Typically, for example, when S is a fluorescer or a chemiluminescer, a quencher is spaced not more than 30 Å away, preferably 1 to 25 Å and more preferably 1 to 20 Å away.

It is intended that, if L is not a bond, then L will be comprised of an aromatic or heteroaromatic ring having 5 to 7 atoms (optionally having 1 to 5 fused rings) wherein a leaving group is bound in a position separated by an even number of ring atoms (e.g. ortho or para in a six-membered aromatic ring) from an OH, SH (thio) or amino nitrogen (including rings amino nitrogens). In such a case L will be further substituted by a group comprised of a modulating group M (when the leaving group comprises S) or a signal group (when the leaving group comprises M). Of course L in such a case can be further substituted as described herein.

In one aspect of the present invention the compound of the formula S-L-M is of the formula:

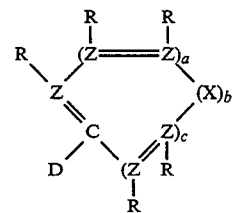

wherein:
X is O, S (sulfur atom), or $NR_1$ wherein $R_1$ is alkyl, H or aryl with the proviso that O or S (sulfur atom) be bound to C atoms,
Z is C or N,
b is 0 or 1,
a and c are 0, 1, or 2 with the proviso that the ring will contain 5 to 7 atoms.
R are independently H or a substitutent having from 1 to 50 atoms other than the requisite hydrogen atoms necessary to satisfy the valencies of such atoms, which atoms are independently selected from the group consisting of carbon, oxygen, nitrogen, sulfur, phosphorus, halogen or two Rs can be taken together to form a ring, being substituted or unsubstituted, a single ring or part of a fused ring system; such substituent can be an electron-withdrawing group as defined herein, an organic group including signal groups S and modulating groups M as defined herein, or an organic group bound through an O or S (sulfur) atom including signal groups S and modulating groups M; wherein one R group selected from OH, SH (thio) and amino nitrogen (including a ring amino nitrogen) is bound to a site separated from D by an even number of ring atoms that do not include X; and D is O or S (sulfur atom) wherein O or S (sulfur atom) is bound to at least one S or M group as defined herein with the proviso that the compound is substantially incapable of reducing the two electron oxidation product of the hydrogen donor back to the hydrogen donor and, as a result, the compound enters into a cleavage reaction with the product. With this proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

In another embodiment of the present invention the compound of the formula S-L-M is of the formula—

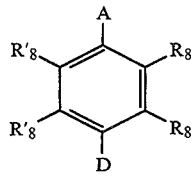

3 wherein:

$R_8$ and $R'_8$ are independently H or a substituent having from 1 to 50 atoms other than the requisite hydrogen atoms necessary to satisfy the valencies of such atoms, which atoms are independently selected from the group consisting of carbon, oxygen, nitrogen, sulfur, phosphorous, halogen or two $R_8$s and/or two $R'_8$s can be taken together to form a ring or rings being substituted or unsubstituted, a single ring or part of a fused ring system; such substituent can be an electron-withdrawing group as defined herein, an organic group including signal groups S and modulating groups M as defined herein, or an organic group including signal groups S and modulating groups M bound through an O or S atom; and A is independently OH, $N(R_9)_2$ or SH (thio), wherein $R_9$ is independently selected from the same group as $R_8$ other than halogen and is bonded to nitrogen at a saturated carbon atom or can be taken together with $R_8$ or $R'_8$ and/or with another $R_9$ to form a ring or rings being substituted or unsubstituted, a single ring or part of a fused ring system, D is O or S (sulfur atom) wherein said O or S (sulfur atom) is bonded to at least one S or M group with the proviso that this compound of the formula S-L-M cannot be substantially oxidized (i.e., the level of oxidation should be sufficiently low so that the predominant reaction will be the cleavage reaction to a quinoid compound by the product of the PAS-catalyzed oxidation of the hydrogen donor.

With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

It is intended that the phrase "$R_8$ and $R'_8$ are independently" indicates that both $R_8$'s and/or both $R'_8$'s can be the same or different. For example, one $R_8$ can be H and the other can be a substituent having from 1 to 50 atoms or one $R_8$ can be a substituent and this other can be a different substituent.

In another aspect of the present invention the compound of the formula S-L-M is selected from the group consisting of 5 or 5'—

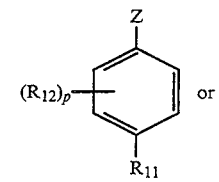

5

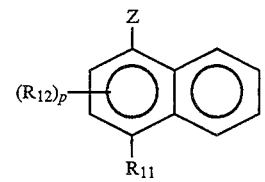

5' wherein:

p is 1 to 4 in 5 and 1 to 2 in 5';

Z is OH, $NH_2$, NH(lower alkyl) or N(lower alkyl)$_2$;

$R_{12}$ is H, lower alkyl, —COOR$_{13}$, —CN, —Cl, —Br, —I, —NO$_2$, —SO$_2$R$_{13}$, —PO$_3$(R$_{13}$)$_2$, —C(O)N(R$_{13}$)$_2$, —SO$_2$N(R$_{13}$)$_2$ wherein $R_{13}$ is independently H, an organic radical including signal or modulating groups, alkyl, carboxyalkyl, amino-substituted lower alkyl, N(lower alkyl)$_2$ or NH(lower alkyl); and $R_{11}$ is —OR$_{14}$ wherein $R_{14}$ is selected from the group consisting of —R$_{15}$, —alkylene—R$_{15}$, —carboxyalkylene—R$_{15}$, —C(O)R$_{15}$, —C(O)N(R$_{15}$)R$_{16}$, —SO$_2$R$_{15}$, —SO$_3$R$_{15}$, P(OR$_{15}$) (OR$_{16}$), PO(OR$_{15}$)(OR$_{16}$) wherein $R_{15}$ is a signal group S or signal modulating group M bound through a carbon atom and $R_{16}$ is an organic group bound through a carbon atom, with the proviso that $R_{12}$ when not H is not in a position ortho to Z when $R_{12}$ is an electron-withdrawing group and Z is OH and that no more than one $R_{12}$ be an electron-withdrawing group. With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

In another aspect of the invention the compound of the formula S-L-M is a compound 7 or 7' of the formula—

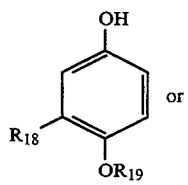 7 or

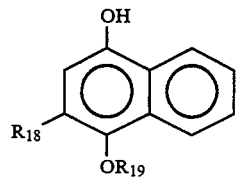 7' wherein:
R$_{19}$ is comprised of a signal generating group S or a signal modulating group M;
R$_{18}$ is H, —COOR$_{19}$, —CN, —Cl, —Br, —I, —NO$_2$, —SOR$_{19}$—, —SO$_2$R$_{19}$—, —PO$_3$(R$_{19}$)$_2$, —C(O)N(R$_{19}$)$_2$, —SO$_2$N (R$_{19}$)$_2$, —C(O)NH(CH$_2$)$_q$N(R$_{20}$)$_2$—C(O)NH(CH$_2$)$_q$NH(CH$_2$)$_2$N(R$_{20}$)$_2$

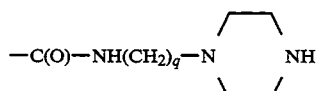

wherein R$_{20}$ is H or lower alkyl and wherein q is independently 1 to 10 and s is 1 to 10. With the proviso that 7 and 7' are further substituted such that . . . With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

In another aspect of the invention the compound of the formula S-L-M is a compound selected from the group consisting of—

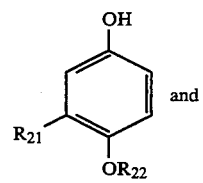 12 and

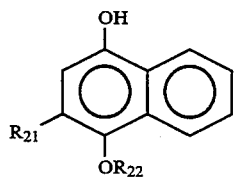 12' wherein R$_{21}$ is H, CN, Cl, or C(O)R$_{23}$ wherein R$_{23}$ is OH, lower alkyl, lower alkoxy, NH$_2$, lower alkylamino, —NH(CH$_2$)$_2$NH (CH$_2$)$_2$NH$_2$, NH(CH$_2$)$_2$N(CH$_3$)$_2$, or

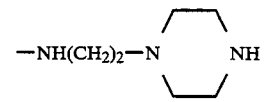

and R$_{22}$ is comprised of a signal generating group S or a signal modulating group M;

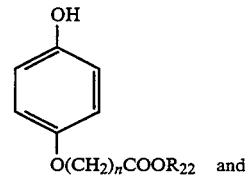 13 and

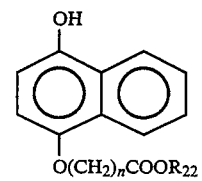 13' wherein n is 1 to 10 and R$_{22}$ is comprised of a signal generating group S or a signal modulating group;

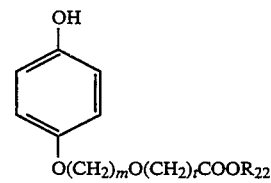 14 wherein m is 1 to 10 and t is 1 to 10 and R$_{22}$ is comprised of a signal generating group S or a signal modulating group M;

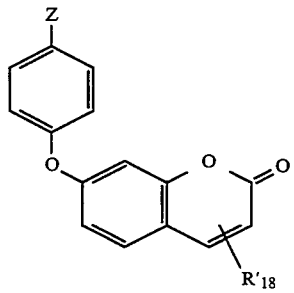 15 wherein Z' is OH or N(R'$_{19}$)$_2$ and R'$_{18}$ is H alkyl aryl or —C(O)X wherein X is OR'$_{19}$ or N(R'$_{19}$)$_2$, and R'$_{19}$ is independently selected from H, an organic radical including signal generating and modulating groups, lower alkyl, or lower alkyl substituted with —COOH, —SO$_3$H or —PO$_3$H; and

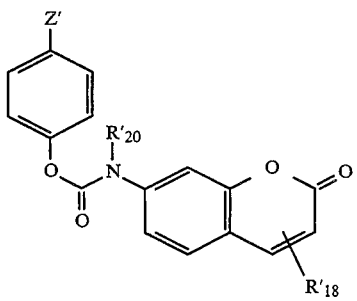

wherein $R'_{18}$ and $Z'$ are defined above and $R'_{20}$ is H or lower alkyl. With the proviso that 12, 12, 13, 13' and 14, as well as 15 and 16 when $12_{19}$ does not comprise a signal generating or modulating group, are further substituted such that . . . With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

Preferred compounds of the formula S-L-M have hydrophilic, usually charged groups that provide water solubility. The products formed on cleavage have solubility properties that depend on the substituents. Therefore, in addition to the signal generating and modulating groups, the substituents on the compounds can be selected so as to impart good water solubility to the reactants but still provide for one or more insoluble cleavage products if this is desirable. For example, by including a positive charge on a phenol compound and a negative charge on a benzidine hydrogen donor, one of the cleavage products will be a zwitterion which will usually be less soluble than either starting component. Also, carboxylic acid groups on the same compounds can lead to a poorly soluble cleavage product because the acidity of one of the carboxyls in the product will usually be lowered and, at the normal pH of the reaction of about 4–6, protonation and charge neutralization can therefore occur.

The compounds may have substituents other than the signal generating and modulating groups and solubility modifying groups. The aromatic ring may be fused to other rings, for example, as in naphthol-based compounds. Also electron donating, electron-withdrawing, or relatively electroneutral substituents can be present. Typical of substituents that have been used are mono-, di-, and tetra-methyl, methoxy, chloro, cyano, carboxy, carboxamido, 3-aminopropylcarboxamide, and carboethoxy. Additional hydroxyl and amino substituents are not desirable. In general, when the compound is a phenol which can be oxidized to a quinone or quinoneimine, it is necessary to include an electron-withdrawing substituent attached to the aromatic ring such as halo, carboxy, nitro, or cyano. Without such a substituent the resulting compound of the formula S-L-M is oxidized by two electrons by the oxidized hydrogen donor thereby fully reducing the latter to the starting hydrogen donor and preventing the cleavage reaction. However, in general, for all compounds of the formula S-L-M the cleavage reaction can only take place if the compound can be oxidized by the oxidized hydrogen donor; but only a one electron oxidation to partially reduce the oxidized hydrogen donor, for example, benzidine to a semiquinone can occur. Thus, when the compound is a phenol with a para leaving group comprising a signal generating or modulating group there will usually be no electron-withdrawing substituent ortho to the phenolic hydroxyl group in order to permit the oxidized hydrogen donor to oxidize the compounds of the formula S-L-M. For a similar reason, it is usually not desirable to include a multiplicity of strong electron-withdrawing substituents in any of the compounds as these groups will increase the oxidation potential and slow the reaction.

Preferred compound of the invention form cleavage products in a yield in excess of 50%, preferably over 90% of the oxidized hydrogen donor, at least during the first observable formation of product. Compounds of the type 12 are particularly useful, especially gentisic acid ($R_{21}$=COOH). Particularly preferred compounds are:

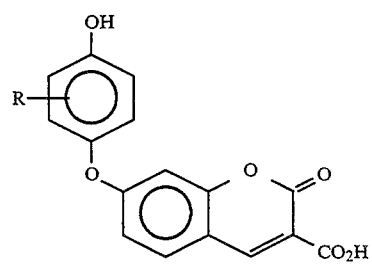

48

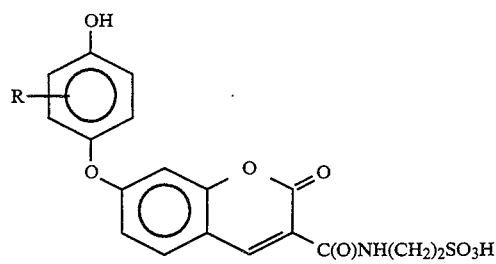

49

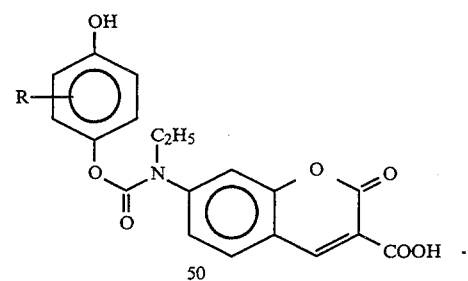

50

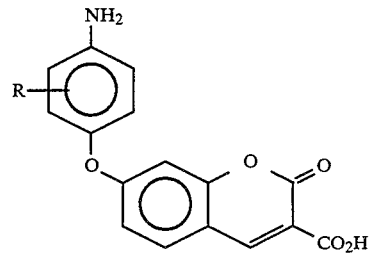

51

52 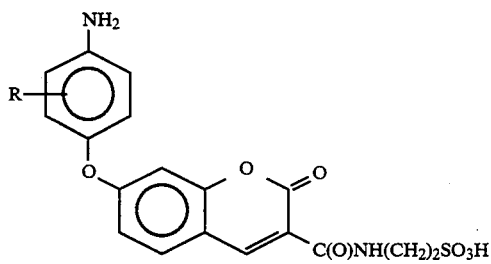

53 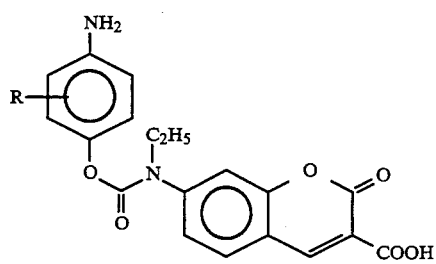

54 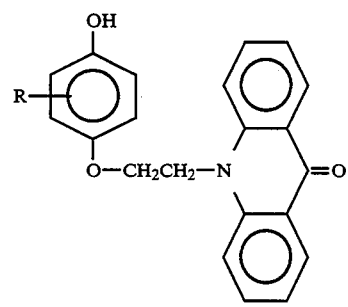

55 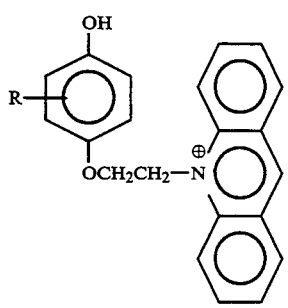

56 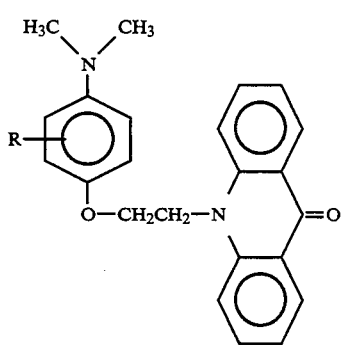

57 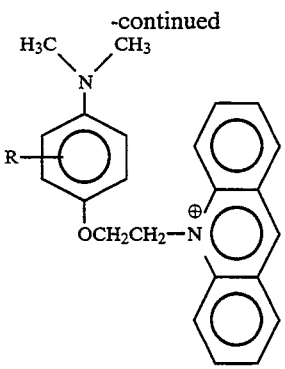

Wherein R is 1 to 4 substituents selected independently from hydrogen or an organic radical including signal modulators. With the proviso that R's be selected such that either one or more R groups comprise a signal modulator or the compound other than the substituted para to the OH group in 48, 49, 50, 54 and 55, the $NH_2$ group in 51, 52 and 53, or the $N(CH_2)_2$ group in 56 and 57 comprises a signal modulator.

Factors which are relevant in determining the efficiency of the compound of the formula S-L-M include, first, the inability of the compound to reduce the oxidized hydrogen donor, generally a benzidine, to this hydrogen donor as determined directly or by separate measurement of the two-electron redox potentials of the hydrogen donor and this compound. If the potential of the compound exceeds that of the hydrogen donor under the experimental conditions of the cleavage reaction, then reduction of the oxidized hydrogen donor should not occur. Second, it is believed that an effective compound will usually be able to undergo one electron oxidation by the oxidized hydrogen donor, generally a benzidine, and the latter must be reduced by one electron to produce a partially reduced hydrogen donor, generally a benzidine semiquinone. Although it is in principle possible to demonstrate by electrochemical methods, such as cyclic voltammetry, that the two half reactions should occur, it is in practice simpler to test directly whether the cleavage reaction will occur. Thus, the presence of a cleavage reaction is taken as positive evidence for the one electron redox reaction. Third, there must be a leaving group containing at least one signal generating on modulating group positioned an even number of ring atoms away from the OH, SH (thio) or amino nitrogen (including ring amino nitrogen) of this compound. Preferably the compound will have an all carbon 6 membered aromatic ring having a leaving group in a para position relative to the OH or amino nitrogen atom substituent. Fourth, the concentration of the compound must be sufficient to assure that the oxidized hydrogen donor will react with the compound without excessive loss due to reaction with unreacted hydrogen donor remaining in the solution.

The selection of efficient compounds, therefore, depends on the hydrogen donor, generally a benzidine, that is used and on selecting compounds that can easily donate only one electron and that have a good leaving group. Usually, the leaving group will be at a strongly nucleophilic center, that is, a center of high electron density in the compound, which is ortho to an electron donating group. The atom of the leaving group bound to this center will usually have a pair of electrons in a non-bonding orbital. The more electronegative the leaving group, the more electron donating the other substituents will have to be in order to provide a nucleophilic center to permit reaction with the oxidized hydrogen donor.

For example, when dicarboxidine is the hydrogen donor, if the leaving group is at least as electronegative as Cl which is quite electronegative, the following compounds are not useful compounds despite the presence of an ortho para electron donating group:

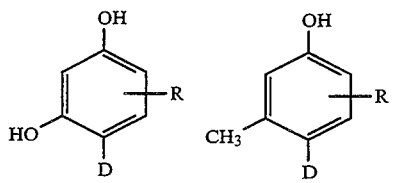

but the following compounds will be useful:

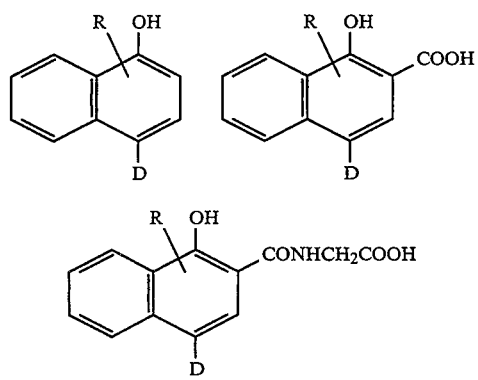

Wherein the R groups are not strongly electron donating or withdrawing. With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S. The ability of the latter group to act as compounds of the formula S-L-M can be attributed to the greater nucleophilicity of the naphthalene nucleus at the low PH (4-6) of the cleavage reaction.

Similarly, the following phenols will not be useful compounds when using dicarboxidine:

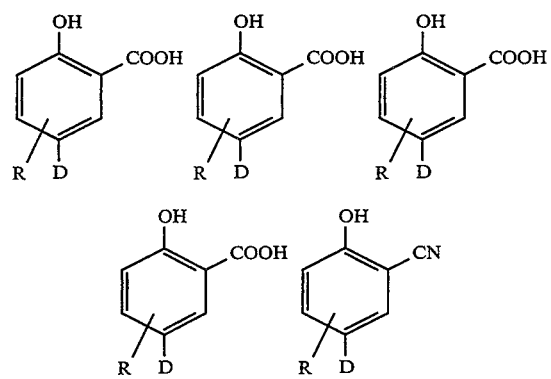

whereas the following compounds will be useful compounds:

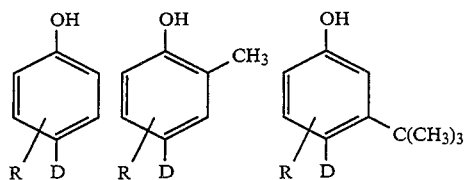

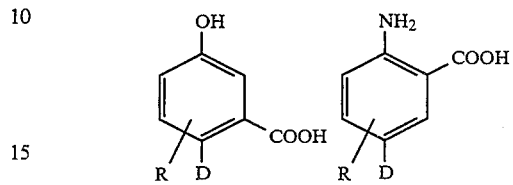

Wherein the R groups are not strongly electron donating or withdrawing. With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S. In this case, the latter group is oxidized by one electron followed by the ready loss of a proton to produce a radical which can couple with the benzidine semiquinone in the case of the phenols, whereas in the former group the radical that is formed following loss of an electron and a proton is stabilized by the ortho substituent and cannot readily couple. By contrast, in the latter group, there is either no stabilizing substituent or, when present, it is in a less stabilizing meta position, or in the case of the highly electron rich amino group, nucleophilic substitution may occur directly or by initial electron transfer without proton loss.

In still another set of examples, the following compounds will not be useful compound because they can be oxidized to quinones by the oxidized dicarboxidine. That is, the phenols have a lower two-electron redox potential than dicarboxidine:

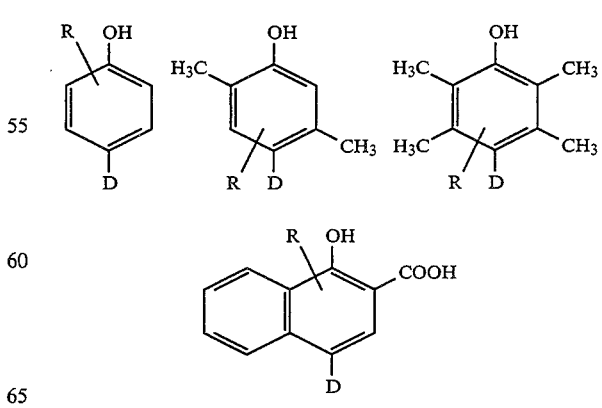

whereas the following hydroquinones that are less readily oxidized will be useful compounds:

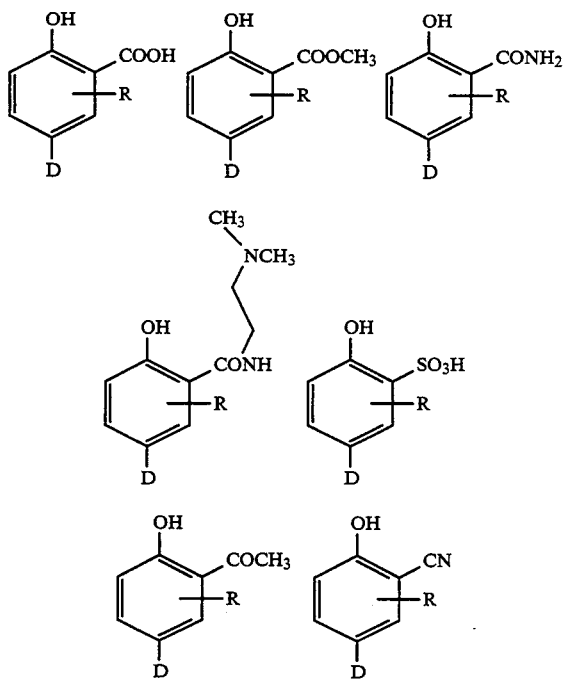

Wherein the R groups are not strongly electron donating or withdrawing. With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

This latter group can also be compared with an additional compound which will not be a useful compound because its redox potential is so high that they it will not oxidized by oxidized dicarboxidine and/or it will be insufficiently nucleophilic.

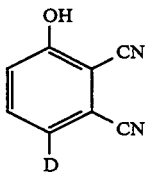

In general, it has been found that compounds whose corresponding oxidized forms have cathodic polarographic half wave potential (relative to the standard calomel electrode or SCE) greater than 0.58 volts will not be compounds useful with dicarboxidine because they are oxidized by oxidized dicarboxidine. When the oxidized compound has a half wave potential between 0.10 and 0.54 volts the corresponding compound will be useful. When the oxidized compound has a half wave potential below 0.1 volt the hydroquinone compound be oxidized it again will not be a compound. See Oldfield, et al., *J. Physical and Colloid Chem.* (1951) 1255 and "Oxidation-Reduction Potentials or Organic Systems" ed. W. M. Clark, chapter 14, page 737 (J. Q. Chambers) published by Williamp and Wilkins, Baltimore (1960).

Compounds that can be utilized in the present invention include derivatives of known compounds that are commercially available and/or can be synthesized by procedures known in the art. Exemplary of various substituted phenols and anilines that have been prepared and their general method of preparation are as follows:

Some general comments follow with regard to compounds that can be utilized in the present invention. Phenols and resorcinols do not trap oxidized dicarboxidine with the same efficiency as para-oxygen-substituted phenols and anilines. Unsubstituted and alkyl-substituted hydroquinones do not trap oxidized dicarboxidine; they actually reduce it. Hydroquinones substituted with two or more electron-withdrawing groups have no effect on oxidized dicarboxidine. Para-methoxy anisole or ortho-methoxy anisole has no effect on oxidized dicarboxidine. Gentisic acid and 2-methoxy-5-hydroxy benzoic acid react with oxidized dicarboxidine, while 2-hydroxy-5-methoxy benzoic acid has no effect on oxidized dicarboxidine.

Analyte—the compound or composition to be measured, the material of interest. The analyte can be a peroxidatively active substance or it can directly or indirectly cause or inhibit peroxidative activity. The analyte can be a member of a specific binding pair (sbp) and may be a ligand, which is mono- or polyvalent, usually antigenic or haptenic, and is a single compound or plurality of compounds which share at least one common epitopic or determinant site. The analyte can also be a component of a particle or can become bound to a particle during an assay. Exemplary of an analyte that is a component of a particle is an antigen on the surface of a cell such as a blood group antigen (A, B, AB, O, D, etc.) or an HLA antigen. Exemplary of an analyte becoming bound to a particle during an assay is an sbp member where a complementary sbp member is bound to a particle, glycoprotein or glycolipids where a lectin is bound to a particle, antibodies where protein A is bound to a particle, and the like. The binding involved when an analyte becomes bound to a particle can be specific or non-specific, immunological or non-immunological.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, and reocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, paparefine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folk acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as attopine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sullenamides, their metabolites and derivatives.

Also included are hormones such as progesterone, testosterone, and so forth.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand-any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Label—A member of the signal producing system that is usually conjugated to an sbp member. The label can be isotopic or non-isotopic, usually non-isotopic, including catalysts such as an enzyme, a chromogen such as a fluorescer, dye or chemiluminescer, a radioactive substance, a particle, and so forth. In the methods of the present invention, at least one label is a peroxidatively active substance.

Signal Producing System—The signal producing system is utilized in assays for analytes and may have one or more components, at least one component being a label. The signal producing system generates a signal that relates to the presence or amount of analyte in a sample. The signal producing system includes all of the reagents required to produce a measurable signal. When the label is not conjugated to an sbp member analogous to the analyte, the label is normally bound to an sbp member complementary to an sbp member that is analogous to the analyte. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by use of electromagnetic radiation, desirably by visual examination.

For purposes of the present invention, the signal-producing system includes at least one active catalyst, usually a peroxidase, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidass, or heterocyclic oxidases, such as uricass and xanthine oxidass, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference.

Non-specific binding—non-covalent binding between substances that is relatively independent of specific surface structures. Such non-specific binding will usually result from charge or electronic interactions between oppositely charged substances. Non-specific binding may also result from hydrophobic interactions between substances.

"Support"—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Sensitivity—is used in the sense of detection limit, i.e., the smallest amount of a peroxidatively active substance, e.g., HRP, giving a signal that is distinguishable from the signal obtained in the absence of the peroxidatively active substance.

Ancillary Materials—various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

The present invention has particular application to the determination of an analyte in a sample suspected of containing such analyte. The present assay method has application both to heterogeneous and homogeneous assays. Exemplary of heterogeneous assays are the radioimmunoassay (RIA, Yalow and Berson, *J. Clin. Invest.* (1960) 39, 1157), and enzyme immunoassays (EIA) such as the enzyme linked immunosorbant assay (ELISA), see "Enzyme-Immunoassay" by Edward T. Maggio, CRC Press Incorporated, Boca Raton, Fla., 1980. Homogeneous immunoassays are exemplified by enzyme multiplied immunoassay techniques (e.g. see U.S. Pat. No. 3,817,837), immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra. The disclosures of the above references are incorporated herein in their entirety.

The assay for a peroxidatively active substance or for an analyte will normally be carried out in an aqueous buffered medium at a moderate pH, generally that which provides optimum sensitivity. The assay can be performed either without separation (homogeneous) or with separation (heterogeneous) of any of the assay components or products.

The aqueous medium may be solely water or may include from 0 to 40 volume percent of a cosolvent. The pH for determination of a peroxidatively active substance is usually about 4 to 6, preferably 4.5–5.5. For maximum color generation and to obtain a precipitable product, a pH of about 4.5 is preferred. For a soluble product, which finds utility in homogeneous assays, a pH of about 5.5 is preferred. However, at higher pH's, the sensitivity of the determination is reduced. Thus, a balance of these factors should determine the particular pH employed. In some circumstances, the reaction can be conducted at a pH of 4 to 6 and detection, such as of fluorescence, can be conducted at pH 7-10, preferably 8 to 9.

The pH for the medium for assays for analytes that are sbp members will usually be in the range of about 4 to 11, more usually in the range of about 5 to 10, and preferably in the range of about 6.5 to 9.5. The pH will usually be a compromise between optimum binding of binding members and the pH optimum for other reagents of the assay such as members of the signal producing system.

Various buffers may be used to achieve the desired pH and maintain the pH during the determination. For the determination of a peroxidatively active substance an alkyl carboxylate buffer such as adipate, citrate, acetate, or the like, is preferred. Numerous other buffers can be employed. Illustrative buffers include borate, phosphate, carbonate, tris, barbital and the like. The particular buffer employed in an assay for an analyte is not critical, but in an individual assay one or another buffer may be preferred. Another factor is the storage stability of the various hydrogen donors and compounds of the formula S-L-M where particular buffers such as adipate may be selected over others to achieve maximum storage stability.

Moderate temperatures are normally employed for carrying out the reactions for determination of a peroxidatively active substance and/or for an sbp member and usually constant temperatures during the period of a measurement are employed. Incubation temperatures will normally range from about 5° to 45° C., more usually from about 15° to 40° C. Temperatures during measurements will generally range from about 10° to 50° more usually from about 15° to 40° C.

As mentioned above, the present invention provides for enhanced sensitivity for the determination of a peroxidatively active substance. The concentration of such substance that may be determined will generally vary from $10^{-19}$M to $10^{-8}$M, more usually from $10^{-16}$M to $10^{-11}$M. The concentration of a hydrogen donor will usually be from $10^{-6}$M to $10^{-2}$M, preferably $10^{-5}$M to $10^{-3}$M. The concentration of a compound of the formula S-L-M will usually be from $10^{-5}$M to $10^{-1}$M, preferably $10^{-5}$M to $10^{-3}$M. The concentration of a hydroperoxide will usually be from $10^{-5}$M to 1M, preferably $10^{-4}$M to $10^{-1}$M.

The concentration of analyte which may be assayed will generally vary from about $10^{-4}$ to $10^{-15}$M, more usually from about $10^{-6}$ to $10^{-14}$M. Considerations, such as whether the assay is qualitative, semiquantitative or quantitative, the particular detection technique and the concentration of the analyte of interest will normally determine the concentrations of the various reagents.

While the concentrations of the various reagents in the medium will generally be determined by the concentration range of interest, the final concentration of each of the reagents will normally be determined empirically to optimize sensitivity. That is, a variation in concentration of the catalyst or of the analyte which is of significance should provide an accurately measurable signal difference.

For immunoassays, while the order of addition of reagents may be varied widely, there will be certain preferences depending on the nature of the immunoassay. The simplest order of addition is to add all the reagents simultaneously. Alternatively, the reagents can be combined sequentially. Optionally, an incubation step may be involved subsequent to each addition, generally ranging from about 30 seconds to 6 hours, more usually from about 2 minutes to 1 hour. Generally, in an assay for an analyte the assay is carried out to the point of determining a signal in relation to the presence of analyte, at which point the reagents for conducting the determination in accordance with the present invention are added. All these reagents must be present at the same time to produce a signal, which is then determined.

The products of the reaction can be monitored by direct observation of the reaction medium, either visually or instrumentally, or a reagent can be added to enhance the detectability of the product as, for example, a higher pH buffer or a hydrophobic surface to enhance the fluorescent signal.

The present invention is exemplified, by way of illustration and not limitation, by a system utilizing dicarboxidine 11 as a benzidine based hydrogen donor and a gentisic acid 17 based compound of the formula S-L-M.

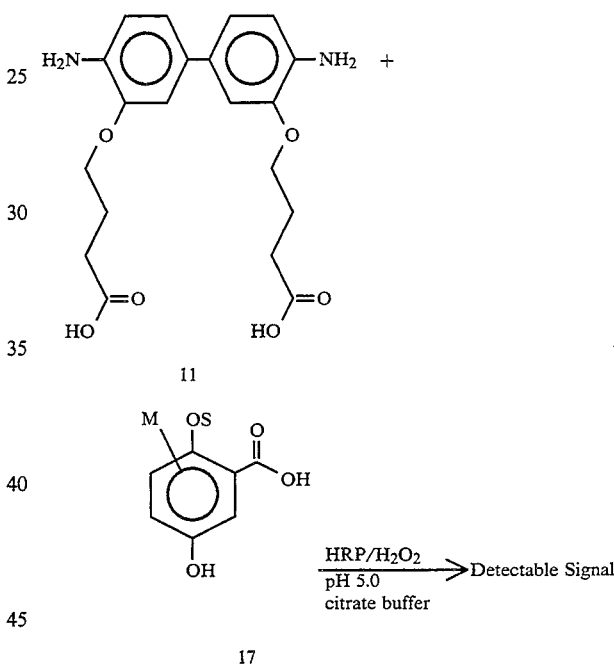

S = Signal Generating Group
M = Signal Modulating Group

The oxidative cleavage reaction of the gentisic acid compound by dicarboxidine forms a product capable of generating a detectable signal. A number of gentisic acid derivatives 34, 35, 36, and 37 were prepared by the reaction of the NHS-ester of gentisic acid with the corresponding amine. In solution, all of these gentisic acid derivatives trapped oxidized dicarboxidine with approximately the same relative rate as gentisic acid 17.

The merocyanine dyes formed from 35, 36, and 37 came out of solution much faster than the merocyanine dye formed from gentisic acid 17. Thus, charge neutralization to enhance precipitability of the resulting dye leads to more precipitable products.

To the extent that any particular theories are referred to herein, the present invention has been demonstrated and should, therefore, not be restricted to any particular theory.

Various specific embodiments employing the methods of the present invention will next be described using dicarboxidine as a benzidine-based hydrogen by way of example and not limitation. Dicarboxidine (11) on oxidation with HRP/$H_2O_2$ will react with, e.g., gentisic acid 17 based compounds of the formula S-L-M to form products capable of generating a detectable signal.

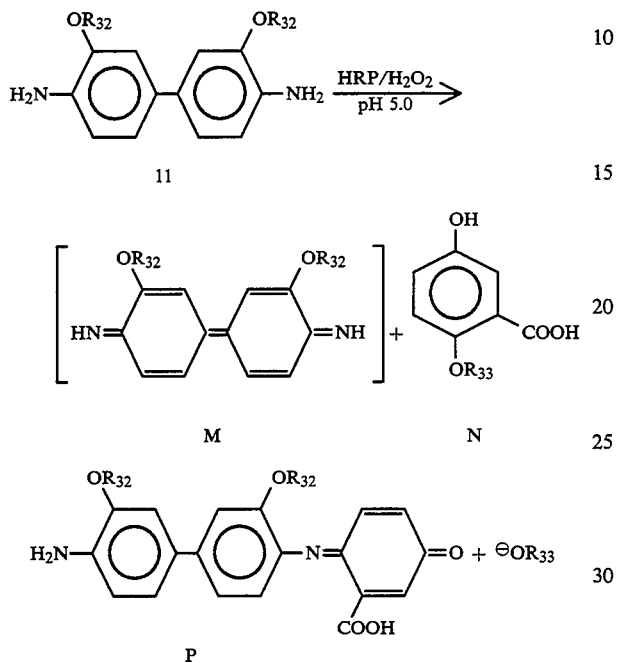

wherein:
$R_{32} = (CH_2)_3\text{—}CO_2H$ and
$R_{33} = $ a fluorophore or chemiluminescer.

The reaction will proceed in almost quantitative yield. $OOR_{33}$ can be a chemiluminescent or a fluorescent species. By the above reaction, a mole of fluorescent moiety is generated per mole of N consumed. The detection of fluorophores is very sensitive. Therefore, by using a fluorophore signal group, an extremely sensitive HRP-labeled detection system is obtained.

Umbelliferone derivatives are exemplary of such fluorophores. Umbelliferone derivatives have been routinely used as fluorescent detection agents for reporter enzymes like i-galactosidase and alkaline phosphatase. Umbelliferone derivatives can be prepared, for example, in a manner similar to that used to prepare umbelliferone derivatives in European Patent Specification 0 060 518. An unsubstituted derivative of 51 was prepared by reacting the anion of umbelliferone with 4-fluoronitrobenzene followed by reduction with Zn/HCl. Unsubstituted 48 was prepared by hydrolysis of diazotized unsubstituted 51.

The HRP assay is preferably conducted at the substrate's most stable formulation and where HRP is most active, i.e., pH 3.5 to 7, preferably about 5.0, and the fluorescence detection is recorded at pH which is dependent on the particular fluorophore and can be in the range of about 4 to 11, preferably about 7 to 9, more preferably about 8. HRP can thus be detected at a level of 1 pg/ml or less of HRP in two minutes.

The present invention may be used in a system involving generation dye product as well as a signal generator of as exemplified (by way of illustration and not limitation) in the following reaction scheme:

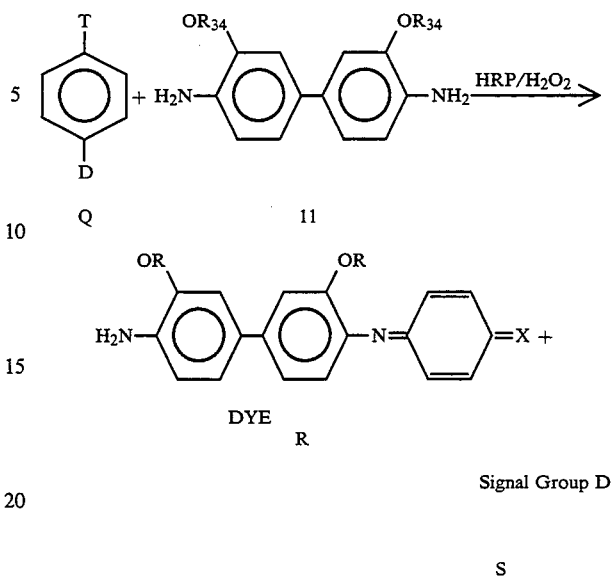

wherein $R_{34}$ is $(CH_2)_3CO_2H$ and T is OH and wherein the R groups are not strongly electron donating or withdrawing. With the proviso that this compound contains both signal generating and signal modulating groups. That is, if the leaving group D comprises a signal group, then R groups are selected such that either an R group comprises M or the portion of this compound other than D comprises M; or, if the leaving group D comprises a modulating group, then R groups are selected such that either an R group comprises S or the portion of the compound other than D comprises S.

Oxidized dicarboxidine reacts regioselectively at the position on the ring of Q para to T. Q is a dye precursor and the cleavage reaction of 0 with 11 gives dye R and signal group D.

One particular embodiment of the present invention involves the detection of molecules such as, e.g., antigens, by means of a sandwich immunoassay. In the method for detection of antigens an immune sandwich complex is formed comprising the antigen, a first antibody (monoclonal or polyclonal) that binds to the antigen and a second antibody that binds to the antigen. Subsequently, the immune sandwich complex is detected and is related to the amount of the antigen analyte in the sample. The immune sandwich complex is detected by virtue of the presence in the complex of a peroxidatively active substance label wherein either or both the first antibody and the second antibody contain labels or substituents capable of combining with labels, such as, for example, linking the antibody to biotin and providing avidin bound to a label.

The immune sandwich complex assays for antigens are well known and protocols for such assays may utilize the present invention. Such sandwich type assays are disclosed in, for example, U.S. Pat. No. 4,486,530, the disclosure of which is incorporated herein by reference in its entirety. The immune sandwich complex assay may be conducted by having the second antibody bound to a support. The immune sandwich complex thus becomes bound to a support if the antigen analyte is present in the sample. The sample suspected of containing the analyte can be combined with the first antibody and the combination subsequently combined with the second antibody. On the other hand, the reagents can be combined simultaneously. After separation of the support from the medium, the support is combined with a peroxide, a hydrogen donor, generally a benzidine, and a compound of the formula S-L-M in accordance with the present invention. A signal is then determined.

Another example of an assay in which the present invention may be employed is described in U.S. Pat. No. 4,879,214. The disclosure of this patent is incorporated herein by reference in its entirety. The method and device are for determining the presence of an analyte in a sample suspected of containing the analyte. The method involves providing in combination a test solution containing the sample, a first member of a specific binding pair and a contact portion of a test strip of bibulous material capable of being traversed by the test solution by means of capillary action. The first member of the specific binding pair can be capable of binding the analyte. The strip contains a second member of a specific binding pair integral therewith for concentrating and non-diffusively binding the first specific binding pair member at a small situs on the strip separated from the contact portion of the strip. The strip can further contain a third sbp member between the small situs and the contact portion. A detectible signal is produced in relation to the presence of the analyte in the test solution. Applying the present invention to the method and device above, the small situs can contain, after the running of the assay, a peroxidatively active substance. A peroxide, a hydrogen donor, generally a benzidine, and a compound of the formula S-L-M are contacted with the situs to generate a signal at the situs as a result of the presence of the peroxidatively active substance, whose presence is related to the presence of the analyte.

To enhance the versatility of the subject invention, the reagents can be provided in packaged combination, in the same or separate containers, in liquid or lyophilized form so that the ratio of the reagents provides for substantial optimization of the method and assay. The kit can comprise a source of a hydroperoxide, a hydrogen donor, generally a benzidine, and a compound as herein described. The kit can further include other separately packaged reagents for conducting an assay including members of other signal producing systems, binding agents such as antibodies, DNA probes, etc. The reagents can be separately contained or one or more can be combined in a single container depending on the cross-reactivity of such reagents.

The present invention also relates to compounds of the formula F-L-Q wherein F is a fluorescer capable of producing a fluorescent signal, Q is a quencher capable of quenching said signal when linked to F, and L is a bond or linking group containing a bond wherein said bond is capable of being cleaved by a reaction of a peroxidatively active substance (PAS) with a substrate of said PAS and a hydrogen donor wherein said cleavage of said bond substantially reduces said quenching. Preferably the bond is contained in a functional group selected from the group consisting of ethers, thioethers, disulfides, esters, amides, and carbonates; the fluorescer is contained in a moiety selected from the group consisting of fluorescein, rhodamine, acridine, rosamine, naphthylamine, coumarin, benzoxazole, benzoxdiazole, anthracene, merocyanine, and perylene moieties; and the quencher is contained in a moiety selected from the group consisting of aniline, phenol, and thiophenol moieties.

A particularly preferred compound of compound of the present invention is a compound of the formula:

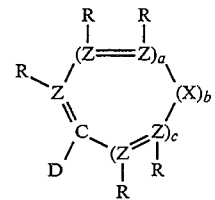

wherein:
X is O, S (sulfur atom), or $NR_1$ wherein $R_1$ is H, alkyl, or aryl, with the proviso that O or S (sulfur atom) be bound to carbon atoms;

Z is C or N;

b is 0 or 1;

a and c are independently 0, 1 or 2 with the proviso that the ring contain 5 to 7 atoms;

R is independently H or a substituent having from 1 to 50 atoms other than hydrogen, which atoms are independently selected from the group consisting of carbon, oxygen, nitrogen, sulfur, phosphorus, and halogen, or two R's can be taken together to form a ring, being substituted or unsubstituted, a single ring or part of a fused ring system, wherein one R is OH, SH (thio), or amino nitrogen bound to a site on the ring, wherein said site is separated from D by an even number of ring atoms excluding X; and D is O or S (sulfur atom) wherein said O or S (sulfur atom) is bonded to F or Q with the proviso that the two electron oxidation potential of said compound of the formula F-L-Q is greater than that of said hydrogen donor.

EXAMPLES

The invention is further described by the following non-limiting illustrative examples. Parts and percentages herein are by weight unless otherwise indicated. Temperatures are in degrees Centigrade (° C).

In the examples, the following abbreviations are used:
DCC—dicyclohexylcarbodiimide
THF—tetrahydrofuran
hr—hour
eq—equivalent
mg—milligram
TLC—thin layer chromatography
$^1$H-NMR—$^1$H nuclear magnetic reconance
IR—infrared
m—multipict
d—doublet
d,d—doublet of doublets
t—triplet
s—singlet
Bu—butyl
EtOAc—ethyl acetate
Me—methyl
TFA—trifluoroacetic acid
DMF—dimethylformamide
MeOH—methyl alcohol
DMSO—dimethylsulfoxide
NHS—N-hydroxysuccinimide
EtOH—ethanol
PSI—pounds per square inch
L.C.—liquid chromatography
F.U.—fluorescence unit
DCU—dicyclohexylurea

EXAMPLE 1

Release of Fluorophore

| Stock Solutions | |
|---|---|
| Compound 49 | 1 mM solution in DMSO |
| Dicarboxidine 11 | 10 mM solution in H₂O |
| 2-chloro-4-diethyl-aminoaniline (XV)* | 10 mM solution in H₂O₂ |
| $H_2O_2$ | 125 mM solution in citrate buffer pH 5.0 (0.1M). Solution made just before use. |
| HRP | The concentration adjusted, based on absorption at 403 nm (e 102 mM$^{-1}$ cm$^{-1}$, - 10 ng/mL and 100 ng/mL (pH 7). |

*For purposes of comparison, not in accordance with the present invention.

(a) pH Jump Method 0.01 mL of dicarboxidine 11 (or XV), 0.1 mL of 49 and 0.04 mL of $H_2O_2$ were added to 0.75 mL (0.76 mL) citrate buffer (pH 5.0, 0.1 M); 0.1 mL of HRP (10 mg/mL) was added to start the reaction. 0.05 mL of this solution was taken every three minutes and added to 0.95 mL of phosphate buffer (pH 8.0, 1.0 M) and spectra recorded. This experiment was repeated.

Results: Fluorescence after 3 minutes - background fluorescence.

|  | 11 + 49 | XV + 49 | 49 |
|---|---|---|---|
| F.U. | 535 | 0.54 | 0.50 |
|  | 552 | 0.55 | 0.50 |

(b) At pH 7.0

0.01 mL of dicarboxidine 11 (or XV), 0.1 mL of 49 and 0.04 mL of $H_2O_2$ were added to 0.75 mL (0.76 mL) of phosphate buffer (0.1M, pH 7.0). 0.1 mL of HRP (100 ng/mL) was added to start the reaction and the spectra recorded. This experiment was repeated.

Results:

|  | 11 + 49 | XV + 49 | 49 |
|---|---|---|---|
| F.U. | 1760 | 220 | 40 |
|  | 1776 | 222 | 40 |

EXAMPLE 2

Sensitivity Measurements

| Stock Solutions |
|---|
| HRP 1 ng/mL |
| $H_2O_2$ 50 Mm |
| citrate buffer pH 4.5 (0.1M) |
| Tris buffer pH 8.3 (1M) |
| Dicarboxidine 10 mM |
| 51 10 mM |
| 48 10 mM |

0.01 mL of dicarboxidine 11, 0.01 mL of 51 or 48 as the the compound of the formula F-L-Q, and 0.04 mL of $H_2O_2$ were added to citrate buffer (pH 4.5, 0.1M). 0.1 mL of the reaction solution was added to 0.9 mL of pH 8.3 (1M Tris buffer, final pH 8.1) and fluorescence recorded at 0, 2, and 5 minutes. The reaction was initiated by adding varying amounts of HRP as shown below in Table 1.

TABLE 1

| Compound (mL) | DCD (mL) | $H_2O_2$ (mL) | HRP (ng/mL) | Buffer[a] (mL) × 10 | F units[b] |
|---|---|---|---|---|---|
| 1. 0.01 | 0.01 | 0.04 | 0.00 | 0.94 | 10 |
| 2. 0.01 | 0.01 | 0.04 | 0.01 | 0.93 | 30 |
| 3. 0.01 | 0.01 | 0.04 | 0.03 | 0.91 | 52 |
| 4. 0.01 | 0.01 | 0.04 | 0.05 | 0.89 | 75 |
| 5. 0.01 | 0.01 | 0.04 | 0.10 | 0.84 | 168 |
| 6. 0.01 | 0.01 | 0.04 | 0.20 | 0.74 | 345 |

[a] pH 4.5
[b] Fluorescence Units

EXAMPLE 3

Preparation of Compound 56

1.97 g of the sodium salt of p-nitrophenol(0.01 mol), 2.16 ml of dibromoethane (0.025 mol) and 0.5g of potassium carbonate were taken in 50 ml of dry acetone (4A activated molecular sieves) and refluxed overnight. Potassium carbonate was filtered and the solvent was removed by rotary evaporation to yield 4-(2-bromoethoxy)nitrobenzene (L) in almost quantitative yield. ¹H-NMR: CDCl w: 365 (t,2H), 44 (t,2H), 70-83 (ABq,4H)/

2.46 g of (0.01 mol) was dissolved in 25 ml of methanol, 5 ml of 37% formaldehyde solution was added. The reaction mixture was hydrogenated under paar apparatus at 60 psi for 4 hours at which time TLC (ethyl acetate) indicated the complete disappearance of starting material. The catalyst was filtered and the filtrate mixed with 500 ml of ethyl acetate and washed with water (5×50 ml). The solvent was removed by rotary evaporation and the product was purified by column chromatography (SiO2, 230–400 mesh, methylene chloride) to yield 1.95 g of pure product 4(2-bromoethoxy)-N,N-dimethylaniline (M).

Yield 80%.

'H-NMR:CDCl₃:w:2.85(S,6H). 3.6(t,2H), 4.25(t,2H), 6.8(ABq4H).

0.39 g of acridone (0.002 mol) and 0.06 g of sodium hydride (0.0025 mol, dry powder, 90%) were taken in 10 ml of dry DMF (CaH, dry) and stirred under argon at 50° C. for 2 hours. At this point the temperature of the oil bath was increased to 80° C. and 0.488 g of M (0.002 mol) was added slowly over 20 minutes. The reaction mixture was stirred under argon for 6 hours at 80° C., at which time TLC (ethyl acetate) indicated the absence of M, therefore the reaction was quenched with water (100 ml), neutralized with dilute acid and the product was extracted into ethyl acetate (50 ml×5). The ethyl acetate fraction was washed with water (50×3), dried over sodium sulphate. The solvent was removed by rotary evaporation and the product was purified by column chromatography (SiO2, 230–400 mesh, methylene chloride:ethyl acetate) to yield 0.23 g of pure product 10-(4-N,N-dimethylanilinoethyl)acridone (56).

Yield 64%,

'H-NMR:CDCl₃:w:1.85(S,6H). 4.4(t,2H), 4.8(t,2H), 6.8(ABq4H), 7.2-7.8(m, 6H) 8.6 (d,d,2H). I.R.: Nujol:cm⁻¹: 2980(m), 1600(m), 1590(m).

EXAMPLE 4

Preparation of Compound 57

36 mgs of 56 (0.1 mmol prepared in Example 18) was taken in 10 ml of dry THF under argon at 5° C. At this point excess of borane in THF (2 ml of 1M solution) was added. The reaction mixture turned bright yellow and was slowly allowed to warm to room temperature over 2 hours. The reaction mixture was added to 50 ml ethyl acetate and washed with brine (5×10 ml). The solvent was removed by rotary evaporation and the product was purified on a preparative TLC plate (silica gel 1000 microns, methylene chloride) 26 mgs of pure product N-(N,N-dimethylanilinoethyl)dihydroacridine (N) was isolated.

Yield 76%.

'H-NMR:CDCl$_3$:w:2.8(S,6H), 3.95(S,2H), 4.3(broad S, 4H), 6.7–7.3(m,12H).

Since N undergoes air oxidation, it was immediately carried over to the next reaction.

69 mgs of N (0.2 retool) was dissolved in 2 ml of acetonitrile (CaH, dry) under argon in an ice bath. 66 mgs of trityl tetrafluoroborate (0.2 mmol) was dissolved in 1 ml of dry acetonitrile and added to 12 slowly over 2 minutes. The reaction mixture was allowed to stir for 10 minutes at which point acetonitrile was removed by rotary evaporation, the green paste was washed with hexane (3×10 ml). the green paste was now applied to a C-18 reverse phase column and eluted with acetonitrile/water (1:9) 7.7 mgs of pure product N-(N,N-dimethylanilinoethyl)acridinium tetrafluoroborate) 57was collected and dried. 57was recrystallized from water as yellow needles.

Yield 89%.

M.P.: 142°–143° C.

Mass spectrum: FAB: M+:343.

'H-NMR:CD$_3$CN:w:2.98(S,6H), 4.74(t,2H), 5.78(t,2H) 6.65–7.15(ABy4H), 7.92 (d,d,2H), 8.46(d,d,2H), 8.5(d,2H), 8.72(d,2H), 9.9(S,1H).

I.R.: THF:cm$^{-1}$:2980(m), 1620(m), 500(m), UV (pH 5.0 titrate buffer 0.1M) 357.6 nm ( 18800 ) 420 nm (4000).

EXAMPLE 5.

Preparation of Compound 54

5.5 g of hydroquinone (0.05 mol) and 3.42 g of benzyl bromide (0.02 mol) along with 1 g of potassium carbonate were refluxed in dry acetone (dried over 4A activated molecular sieves) for 24 hours. The reaction mixture was poured into 500 ml of water, neutralized with dilute acid and extracted into methylene chloride (5×50 ml). The solvent was removed by rotary evaporation and the product was purified by column chromatography (SiO2, 230–400 mesh, methylene chloride) to yield 3.6 g of product 4-benzyloxyphenol (P).

Yield 90% based on benzyl bromide.

'H-NMR:CDCl$_3$:w:5.0(S,3H), 6.8(ABy,4H), 7.45(m,5H).

2 g of E (0.01 mol) and excess of 1,2-dibromoethane (5 g) were taken in 100 ml of dry acetone (dried over 4A activated molecular sieves) containing 1 g of potassium carbonate. The reaction mixture was refluxed under argon for 48 hours at which time potassium carbonate was filtered and acetone was mixed with 500 ml of ethyl acetate and washed with water (5×50 ml). The solvent was removed by rotary evaporation and the product was purified by column chromatography (SiO2, 230–400 mesh, methylene chloride) to yield 2.6 g of product 4-benzyloxy-1-(2-bromoethoxy)benzene (O)

Yield 85%.

'H-NMR:CDCl$_3$:w:3.6(t,2H), 4.2(t,2H), 5.0(S,2H) 6.8 S (ABq, 4H), 7.4 (m, 5H).

0.39 g of acridone (0.002 mol) and 0.06 g of sodium hydride (0.0025 mol, dry powder, 90%) were taken in 10 ml of dry DMF (CaH, dry) and stirred under argon at 50° C. for 2 hours. At this point, the temperature of the oil bath was increased to 90° C. and 0.614 g of O (0.002 mol) was added slowly over 20 minutes. The reaction mixture was stirred under argon for 6 hours at 90° C. at which time TLC (ethylacetate) indicated the absence of Q; therefore, the reaction was quenched with water (100 ml), neutralized with dilute acid and the product was extracted into ethyl acetate (50 ml×5). The ethyl acetate fraction was washed with water (50 ml×3), dried over sodium sulphate. The solvent was removed by rotary evaporation and the product was purified by column chromatography (SiO2, 230–400 mesh, methylene chloride: ethyl acetate (5:1)) to yield 0.24 g of pure product N-(benzyloxyphenoxyethyl)acridone Yield 56%, 'H-NMR:CDCl$_3$:w:4.4(t,2H), 4.8(t,2H), 5.0(S,2H) 6.9 (ABy,4H), 7.4–8.0(m,eH), S.5(d,d,2H).

I.R.: Nujol:cm$^{-1}$:2980(m), 1600(S), 1500(m), 1490(m).

0.084 g of E (0.2 mmol) was dissolved in 5 ml of ethanol and 2 ml of acetone, 0.005 g of Pd/C (10%) was added to it and the solution is hydrogenated under paar apparatus at 20 psi for 4 hours, at which time TLC (methylene chloride) indicated the complete disappearance of starting material. The catalyst was filtered and the solution is taken in 200 ml of ethyl acetate and washed with brine (50 ml×5). The solvent was removed by rotary evaporation and the product was purified on a preparative TLC plate (silica gel, 1000 microns, ethyl acetate) to yield 0.05 g of pure product N-4-hydroxyphenoxyethylacridone Yield 76%.

'H-NMR:CDCl$_3$:w:4.4(t,2H), 4.8(t,2H), 6.7 (ABq,4H), 7.6–8.0(m,6H), 8.5(d,d,2H).

I.R.: Nujol:cm$^{-1}$:3400(w), 2980(m), 1620(m), 1590(m), 1500(m).

EXAMPLE 6

Preparation of Compound 55

33 mgs of 54 (0.1 mmol) (prepared in Example 20) was taken in 10 ml of dry THF under argon at 5° C. At this point excess of borane in THF (2 ml of 1M solution) was added. The reaction mixture turned bright yellow and was slowly allowed to warm to room temperature over 2 hours. The reaction mixture was added to 50 ml ethyl acetate and washed with brine (5×10 ml). The solvent was removed by rotary evaporation and the product was purified on a preparative TLC plate (silica gel, 1000 microns, methylene chloride). 24 mgs of pure product N-4-hydroxyphenoxyethyldihydroacridine (S) was isolated.

Yield 75%.

'H-NMR:CDCl$_3$:w:3.95(S,2H), 4.3(broad S,4H), 6.7–7.3 (m,12H).

As the product (6) undergoes air oxidation, it was immediately carried over to the next reaction.

I.R.: THF:cm$^{-1}$: 3500(m), 2980(m), 2900(m), 1620(m), 1500(s), 440(s),

UV (pH 5.0 citrate buffer 0.1M): 357 nm (13600), 420 nm (2700).

32 mgs of S (0.1 mmol) was dissolved in 2 ml of acetonitrile (CaH, dry) under argon in an ice bath. 33 mgs of trityl tetrafluoroborate (0.1 mmol) was dissolved in 1 ml of dry acetonitrile and added to S slowly over 2 minutes. The reaction mixture was allowed to stir for 10 minutes at which point acetonitrile was removed by rotary evaporation, the green paste was washed with hexane (3×10 ml). the green paste was applied to a C-18 reverse phase column and eluted with acetonitrile/water (1:9). 35 mgs of pure product N-(4-hydroxyphenoxyethyl) acridinium tetrafluoroborate 55 was collected and dried. 7 was recrystallized from water as dark yellow needle shaped crystals.

Yield 87%.

M.P.: 267°-268° C.

Mass spectrum: FAB: M+-316

'H-NMR: (CD$_3$CN) :w:4.66(t,2H), 5.73 (t, 2H), 6.5(s, 1H, phenolic O—H), 6.6(ABq,4H), 7.98(d,d,2H), 8.42(d,d,2H), 8.52(d,2H), 8.72(d,2H), 9.9(S,1H).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Each of the references referred to above is incorporated in its entirety by reference thereto.

What is claimed is:

1. A kit for detecting a peroxidatively active substance (PAS) in a sample or medium suspected of containing said PAS, said kit comprising in packaged combination:

a compound of the formula F-L-Q wherein F is a fluorescer capable of producing a fluorescent signal, Q is a quencher capable of quenching by energy transfer said signal when linked to F, and L is a bond or linking group containing a bond wherein said bond is capable of being cleaved by an oxidation-reduction reaction of said PAS with a substrate of said PAS and a hydrogen donor wherein said cleavage substantially reduces said quenching; and a hydrogen donor.

2. The kit of claim 1 wherein said bond is contained in a functional group selected from the group consisting of ethers, thioethers, disulfides esters, amides, and carbonates.

3. The kit of claim 1 wherein said fluorescer is contained in a moiety selected from the group consisting of fluorescein, rhodamine, acridine, rosamine, naphthylamine, coumarin, benzoxazole, benzoxdiazole, anthracene, merocyanine, and perylene moieties.

4. The kit of claim 1 wherein said peroxidatively active substance is selected from the group consisting of complexed transition metal ions, hemes, hemoproteins, and peroxidases.

5. The kit of claim 1 wherein said quencher is contained in a moiety selected from the group consisting of aniline, phenol, and thiophenol moieties.

6. The kit of claim 1 wherein said F-L-Q is of the formula:

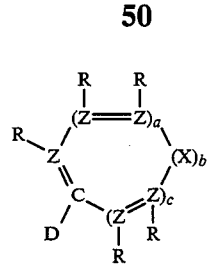

wherein:

X is O, S (sulfur atom), or NR$_1$ wherein R$_1$ is H, alkyl, or aryl, with the proviso that O or S (sulfur atom) be bound to carbon atoms;

Z is C or N;

b is 0 or 1;

a and c are independently 0, 1 or 2 with the proviso that the ring contain 5 to 7 atoms;

R is independently H or a substituent having from 1 to 50 atoms other than hydrogen, which atoms are independently selected from the group consisting of carbon, oxygen, nitrogen, sulfur, phosphorus, and halogen, or two R's can be taken together to form a ring, being substituted or unsubstituted, a single ring or part of a fused ring system, wherein one R is OH, SH (thio), or amino nitrogen bound to a site on the ring, wherein said site is separated from D by an even number of ring atoms excluding X; and D is O or S (sulfur atom) wherein said O or S (sulfur atom) is bonded to F or Q with the proviso that the two electron oxidation potential of said compound of the formula F-L-Q is greater than that of said hydrogen donor.

7. The kit of claim 1 wherein said hydrogen donor is selected from the group consisting of benzidines, p-aminophenols, 4-aminoantipyrenes, and p-phenylenediamines.

8. The kit of claim 1 wherein said hydrogen donor is of the formula:

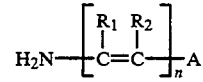

wherein:

A is a hydroxyl group, an amino group, —NHR$_3$, or —NR$_3$R$_4$, wherein R$_3$ and R$_4$ are independently an alkyl group having 1 to 5 carbon atoms, a cycloalkyl group having 3 to 6 carbon atoms, a hydroxyalkyl group having 1 to 5 carbon atoms, or an acylaminoalkyl group having 1 to 5 carbon atoms; or R$_3$ and R$_4$ may combine to form a ring which is unfused or fused, substituted or unsubstituted, a single ring, or part of a multi-ring system;

R$_1$ and R$_2$ are independently a hydrogen atom, an alkyl group having 1 to 5 carbon atoms, an alkoxy group having 1 to 5 carbon atoms, a halogen atom, a carboxyl group, a methanesulfonyl group or a phenyl group; or R$_1$ and R$_2$ may combine together to form a cycloalkene, an aromatic ring or a heterocyclic ring; and n is 1 to 5.

* * * * *